(12) United States Patent
Horsager et al.

(10) Patent No.: US 8,457,754 B2
(45) Date of Patent: Jun. 4, 2013

(54) APPARATUS AND METHOD FOR ELECTRICAL STIMULATION OF HUMAN NEURONS

(75) Inventors: Alan Matthew Horsager, Los Angeles, CA (US); Scott H. Greenwald, Seattle, WA (US); Mark S. Humayun, Glendale, CA (US); Matthew J. McMahon, Los Angeles, CA (US); Ione Fine, Seattle, WA (US); Robert J. Greenberg, Los Angeles, CA (US); Geoffrey M. Boynton, Seattle, WA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1151 days.

(21) Appl. No.: 11/952,051

(22) Filed: Dec. 6, 2007

(65) Prior Publication Data

US 2008/0125832 A1    May 29, 2008

Related U.S. Application Data

(63) Continuation-in-part of application No. 11/818,373, filed on Jun. 14, 2007.

(60) Provisional application No. 60/814,308, filed on Jun. 16, 2006, provisional application No. 60/872,098, filed on Dec. 1, 2006, provisional application No. 60/872,099, filed on Dec. 1, 2006, provisional application No. 60/872,101, filed on Dec. 1, 2006, provisional application No. 60/873,208, filed on Dec. 6, 2006.

(51) Int. Cl.
*A61N 1/08* (2006.01)

(52) U.S. Cl.
USPC .................................. 607/54; 607/53

(58) Field of Classification Search
USPC .............................. 607/53, 54, 115
See application file for complete search history.

(56) References Cited

U.S. PATENT DOCUMENTS

| | | | |
|---|---|---|---|
| 5,052,024 A * | 9/1991 | Moran et al. ................... | 375/219 |
| 5,109,844 A | 5/1992 | de Juan, Jr. et al. | |
| 5,166,749 A * | 11/1992 | Curbelo et al. ................ | 356/452 |
| 5,935,155 A | 8/1999 | Humayun et al. | |
| 5,944,747 A | 8/1999 | Greenberg et al. | |
| 6,400,989 B1 | 6/2002 | Eckmiller | |
| 6,458,157 B1 | 10/2002 | Suaning | |
| 6,718,209 B2 | 4/2004 | Williamson et al. | |
| 6,745,155 B1 * | 6/2004 | Andringa et al. ............. | 702/189 |
| 6,974,533 B2 | 12/2005 | Zhou | |

(Continued)

FOREIGN PATENT DOCUMENTS

| WO | WO 00/56393 | 9/2000 |
|---|---|---|
| WO | WO 03/076011 A1 | 9/2003 |

OTHER PUBLICATIONS

Donaldson, Gail S. et al. "Psychometric functions and temporal integration in electric hearing." J. Acoustic Soc. Am. 101 (6), Jun. 1997. pp. 3706-3721.*

*Primary Examiner* — Allen Porter, Jr.
(74) *Attorney, Agent, or Firm* — Scott B. Dunbar

(57) ABSTRACT

An apparatus and method for retinal stimulation are shown. The method comprises varied parameters, including frequency, pulse width, and pattern of pulse trains to determine a stimulation pattern and neural perception threshold, and creating a model based on the neural perception thresholds to optimize patterns of neural stimulation.

19 Claims, 26 Drawing Sheets

U.S. PATENT DOCUMENTS

| | | |
|---|---|---|
| 2002/0091421 A1* | 7/2002 | Greenberg et al. ............ 607/54 |
| 2003/0181957 A1 | 9/2003 | Greenberg et al. |
| 2004/0127957 A1* | 7/2004 | Fujikado et al. ............... 607/54 |
| 2004/0176821 A1 | 9/2004 | Delbeke et al. |
| 2004/0193670 A1* | 9/2004 | Langan et al. ............... 708/819 |
| 2004/0236389 A1 | 11/2004 | Fink et al. |
| 2005/0055069 A1* | 3/2005 | Franck ............................ 607/62 |
| 2005/0222624 A1 | 10/2005 | Greenberg et al. |
| 2005/0228647 A1* | 10/2005 | Fisher ............................ 704/205 |
| 2006/0129207 A1 | 6/2006 | Fried et al. |
| 2007/0142877 A1* | 6/2007 | McLean ........................ 607/54 |

* cited by examiner

Q: DID YOU SEE STIMULUS? (YES/NO)

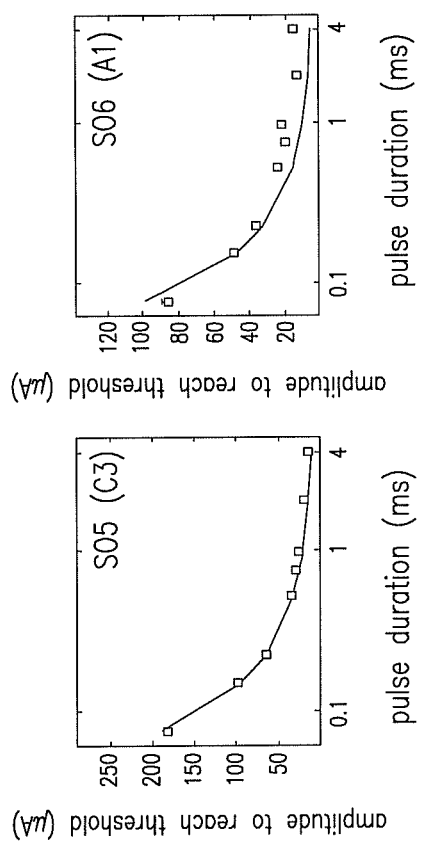
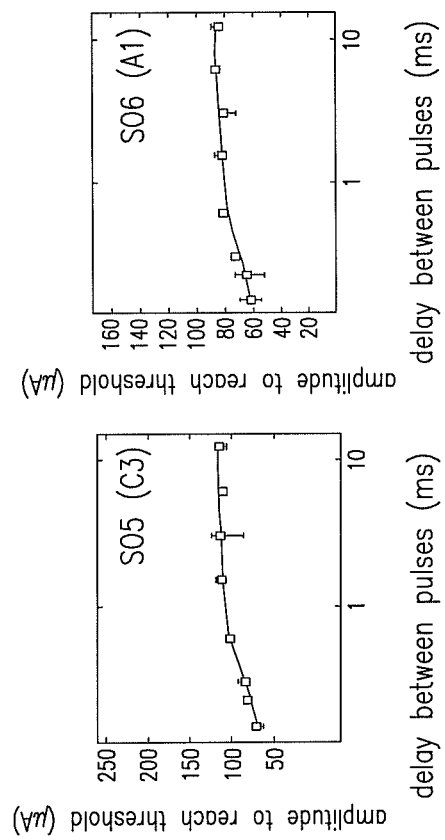
FIG. 21A
FIG. 21B

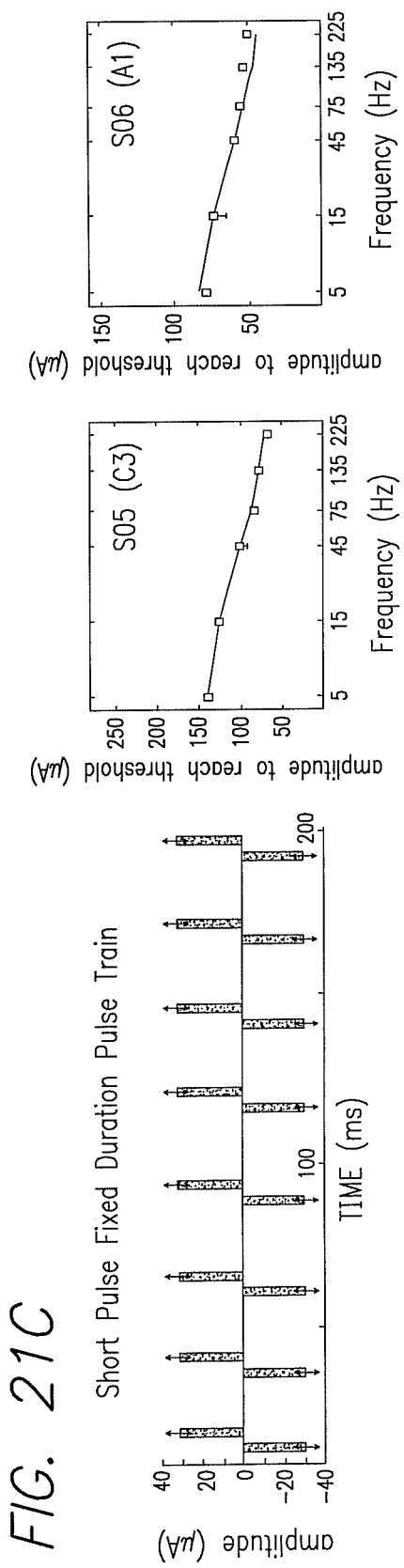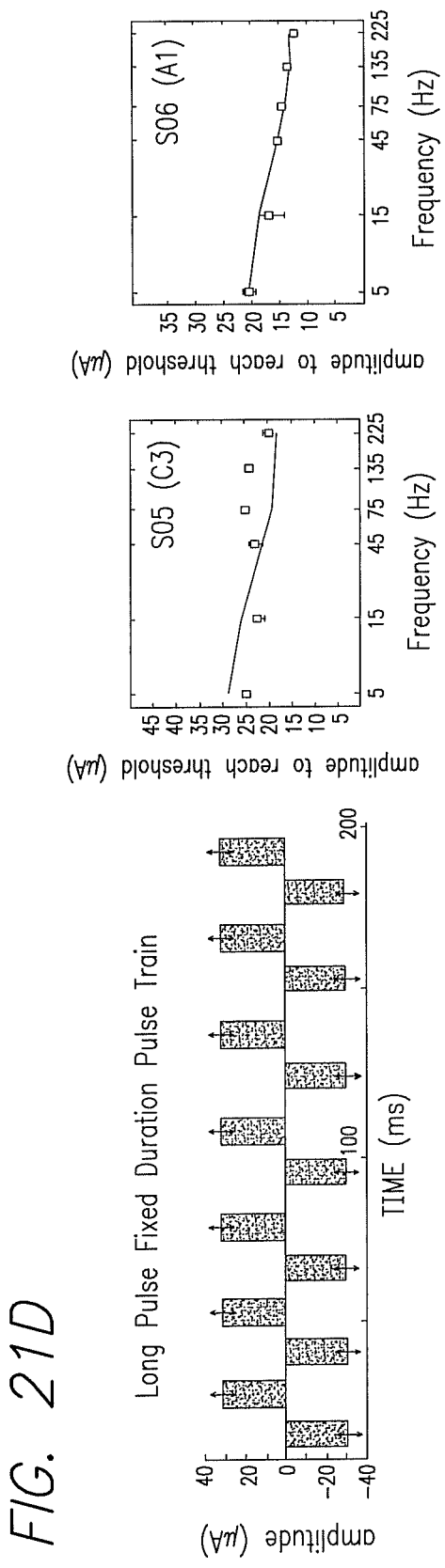
FIG. 21C
FIG. 21D

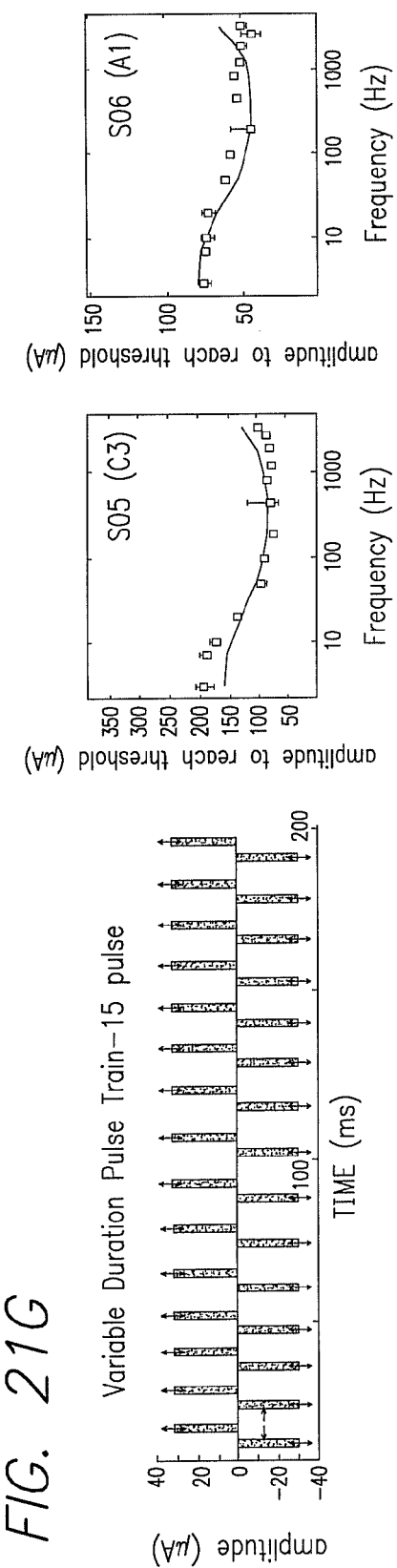
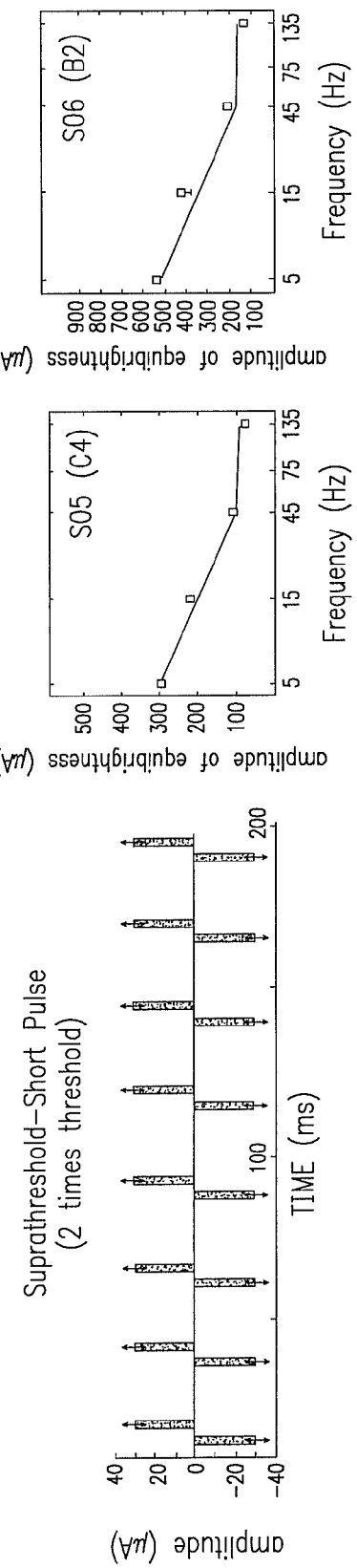
FIG. 21G
FIG. 22A

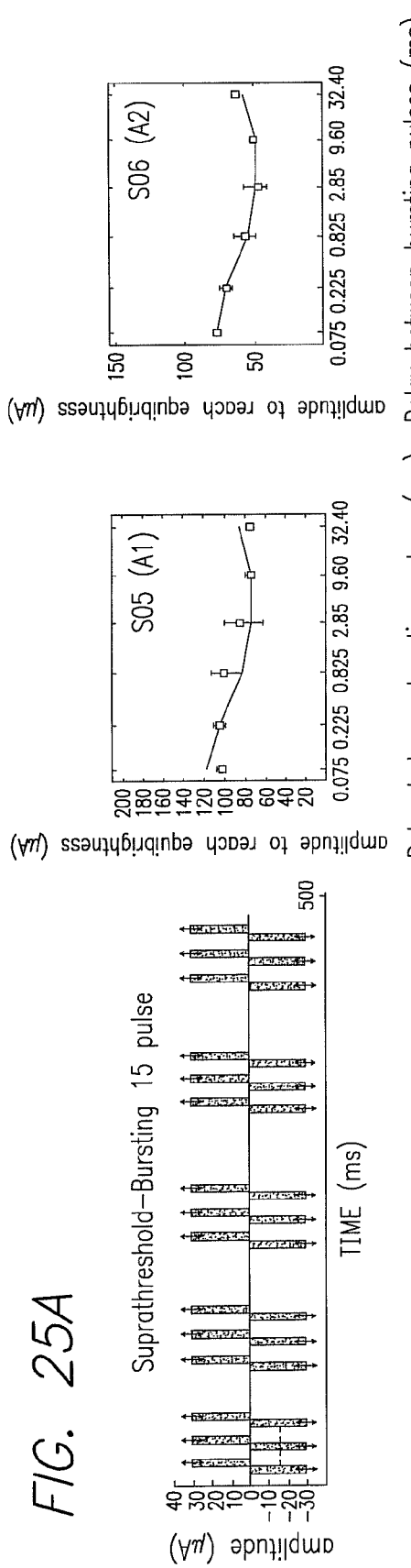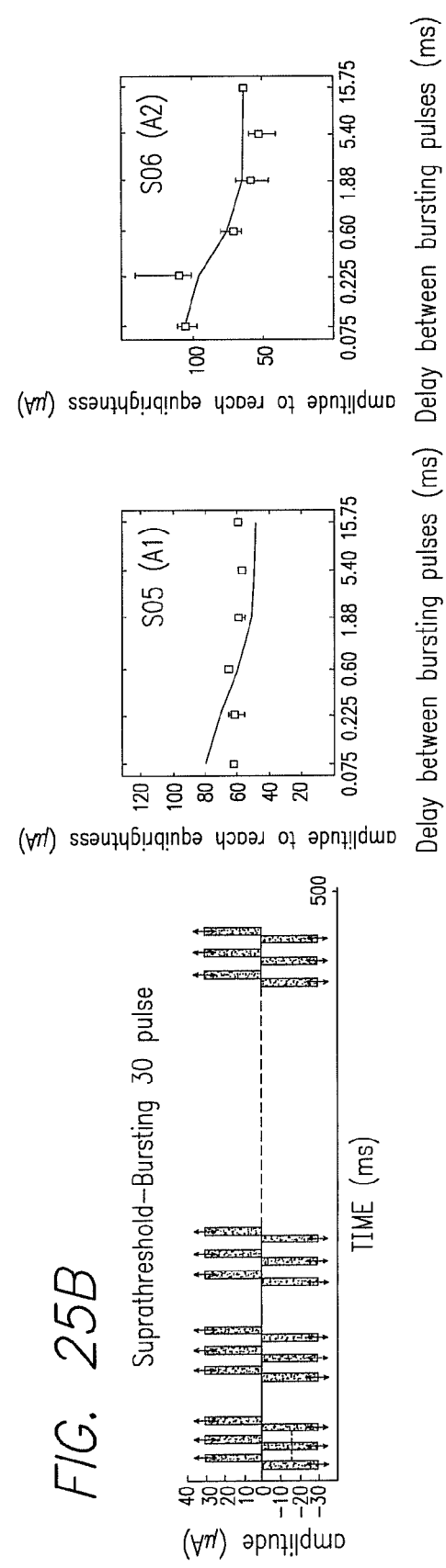
FIG. 25A
FIG. 25B

APPARATUS AND METHOD FOR ELECTRICAL STIMULATION OF HUMAN NEURONS

CROSS REFERENCE TO RELATED APPLICATIONS

This application is a continuation-in-part of U.S. application Ser. No. 11/818,373 filed Jun. 14, 2007 for A Method for Stimulation of the Human Retina Using Pulse Trains, which claims priority to U.S. Provisional Ser. No. 60/814,308 for "Human Retinal Electrical Stimulation Using Pulse Trains" filed on Jun. 16, 2006, U.S. Provisional Ser. No. 60/872,098 for "Evidence For Synchrony Using Direct Electrical Stimulation Of The Human Retina" filed on Dec. 1, 2006; U.S. Provisional Ser. No. 60/872,099 for "A Model Of Temporal Integration During Electrical Stimulation Of The Human Retina" filed on Dec. 1, 2006; U.S. Provisional Ser. No. 60,872,101 for "Selective Adaptation Using Electrical Stimulation In Humans" filed on Dec. 1, 2006; and U.S. Provisional Ser. No. 60/873,208 for "A Model Of Temporal Integration During Electrical Stimulation Of The Human Retina" filed on Dec. 6, 2006, all of which are incorporated herein by reference in their entirety.

GOVERNMENT RIGHTS NOTICE

This invention was made with government support under grant No. R24EY12893-01, awarded by the National Institutes of Health. The government has certain rights in the invention.

FIELD

The present disclosure is generally directed to neural stimulation and more specifically to an apparatus and method for providing intensity control.

BACKGROUND

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., de Juan, et al., 99 μm. J. Ophthalmol. 272 (1985). These retinal tacks have proved to be biocompatible and remain embedded in the retina, with the choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY

The present disclosure relates to an apparatus and method for retinal stimulation wherein the apparatus allows for the placement of a prosthetic device on the inner retinal surface to provide artificial sensations including vision; and wherein visual perception threshold is determined and stimulation parameters are varied, including frequency, pulse width, and pattern of pulse trains.

According to a first embodiment of the present disclosure, a retinal stimulation method is provided, comprising: generating a stimulation pattern by stimulating a retina of a patient with an impulsive electrical signal; and determining how visual perception depends on the generated stimulation pattern by observing perceptual threshold as a function of features of the impulsive electrical signal.

According to a second embodiment of the present disclosure, a method for determining visual perceptual threshold is provided, comprising: exposing subjects to a series of variable current stimuli; decreasing amplitude of the variable current stimuli if subject answers correctly to a current stimulus; increasing amplitude of the current stimuli if subject answers incorrectly to the current stimulus; and generating a psychometric function based on answers of the subject, wherein a yes-no paradigm is used, and half of the series of variable current stimuli contained no stimulus.

According to a third embodiment of the present disclosure, a method for determining visual perceptual threshold is provided, comprising: exposing subjects to a series of variable current stimuli; decreasing amplitude of the variable current stimuli if subject answers correctly to a current stimulus; increasing amplitude of the current stimuli if subject answers incorrectly to the current stimulus; and generating a psychometric function based on answers of the subject, wherein the variable current stimuli are varied in a 3 up-1 down staircase pattern.

According to a fourth embodiment of the present disclosure, a retinal stimulation apparatus is provided, comprising: means for generating a stimulation pattern by stimulating a retina of a patient with an impulsive electrical signal; and means for determining how visual perception depends on the generated stimulation pattern by observing perceptual threshold as a function of features of the impulsive electrical signal.

According to a fifth embodiment of the present disclosure, a visual prosthetic apparatus for retinal stimulation is provided comprising an implantable portion and an external portion, wherein the implantable portion comprises a cable, an RF receiver, an inductive coil and an array of electrodes, for stimulating visual neurons, and the external portion comprises a frame, a camera, an external coil and a mounting system for the external coil.

According to a sixth embodiment of the present disclosure, a retinal stimulation device is provided, comprising: a stimulation pattern generator to provide a signal to a retina, wherein the stimulation pattern generator generates an impulsive electrical signal comprising a pulse train of biphasic pulses, the pulse train having a delay between pulses and a pulse train frequency.

According to a further embodiment of the present disclosure, an apparatus or device for performing any of the method claims of the present disclosure, alone or in combination, is disclosed.

Further embodiments are disclosed throughout the specification, drawings and claims of the present disclosure.

BRIEF DESCRIPTION OF THE DRAWINGS

FIG. 21A-G is a series of bar charts and response graphs where each row contains an example of the pulse train stimulus and data with model predictions from the constrained model.

DETAILED DESCRIPTION

Figure 1:
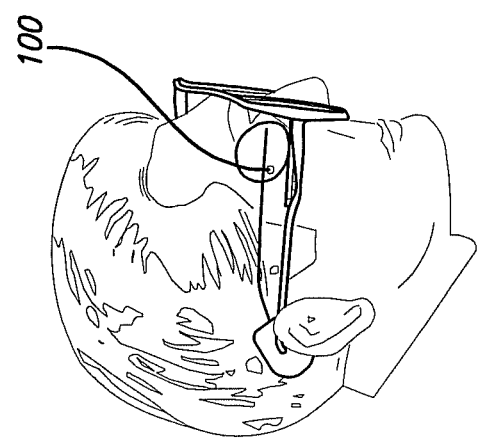
FIG. 1 is a brief schematic view of an implanted visual prosthesis.

FIG. 1 is a schematic view of a prosthesis for stimulating retinal cells. Patients suffering from retinitis pigmentosa (RP) sustain severe vision loss as a result of photoreceptor death. In the preferred prosthesis, the electrode array is aligned in a 4×4 matrix implanted epiretinally, which covers about 10 degrees of visual angle. The upper sub figure shows a schematic of an electrode array in a 4×4 configuration. The subfigure from this schematic details a graphic representation of the system of neural cells under each electrode, wherein the neural cells shown are no longer organized, but unorganized with significant cell death.

Figure 2:
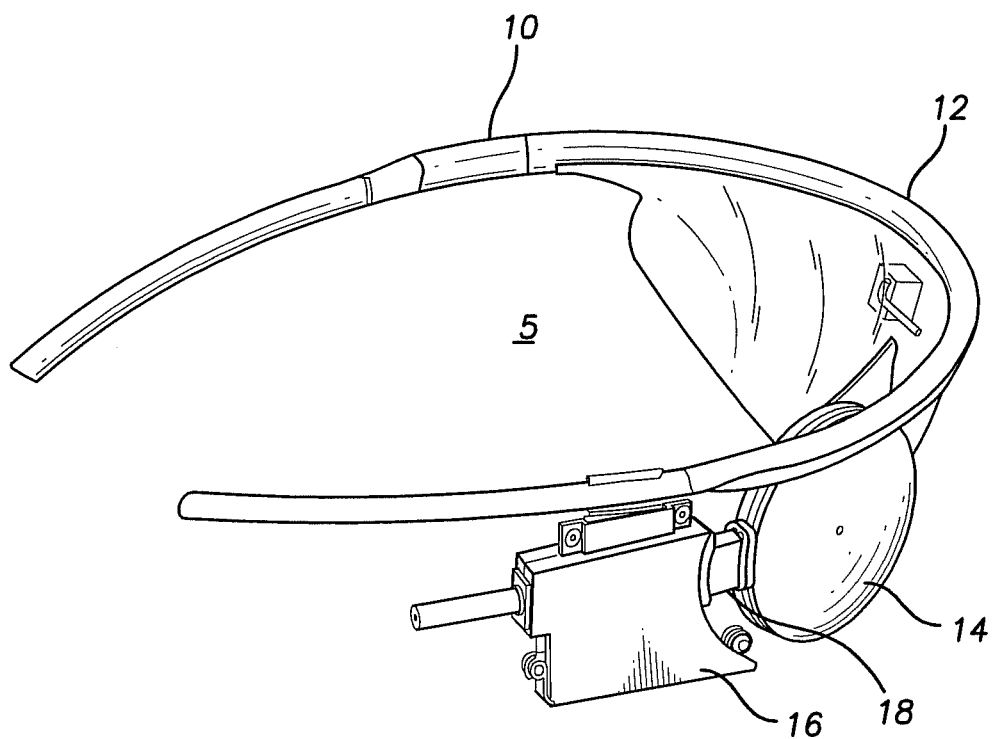
FIG. 2 is a prospective view of a visual prosthesis.
Figure 3:
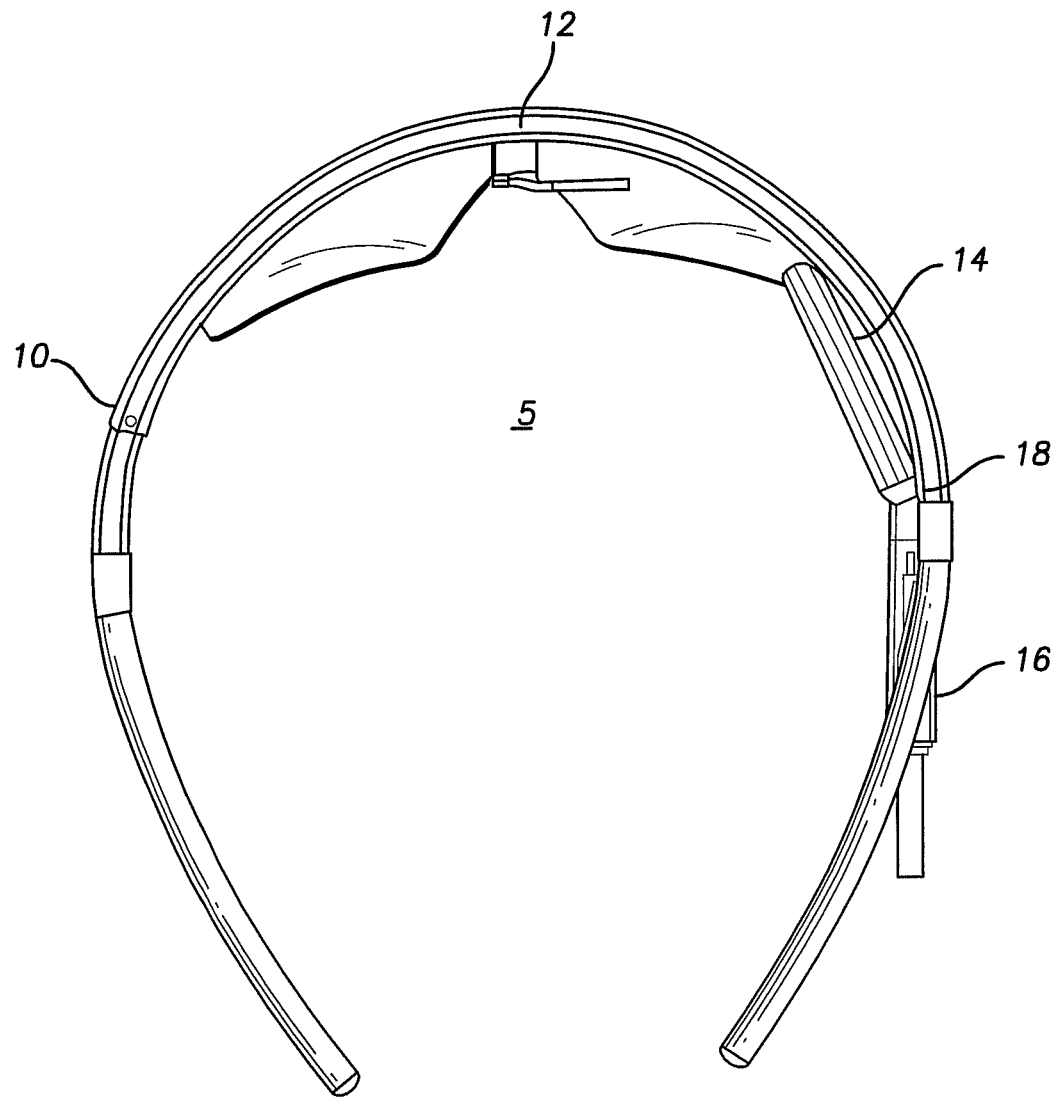
FIG. 3 is a top view of the visual prosthesis shown in FIG. 2.
Figure 4:
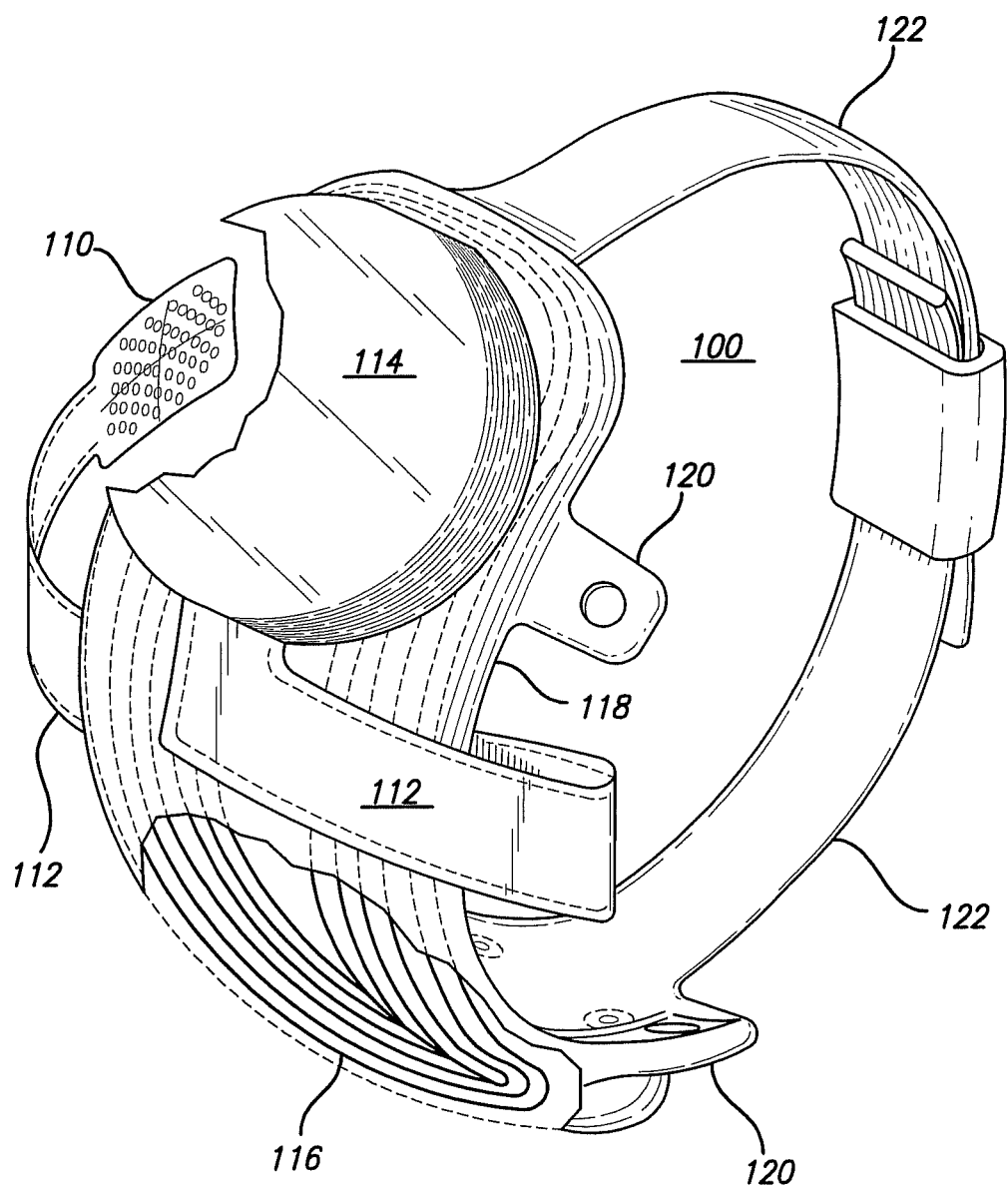
FIG. 4 is a perspective view of the implantable portion of a visual prosthesis.
Figure 5:
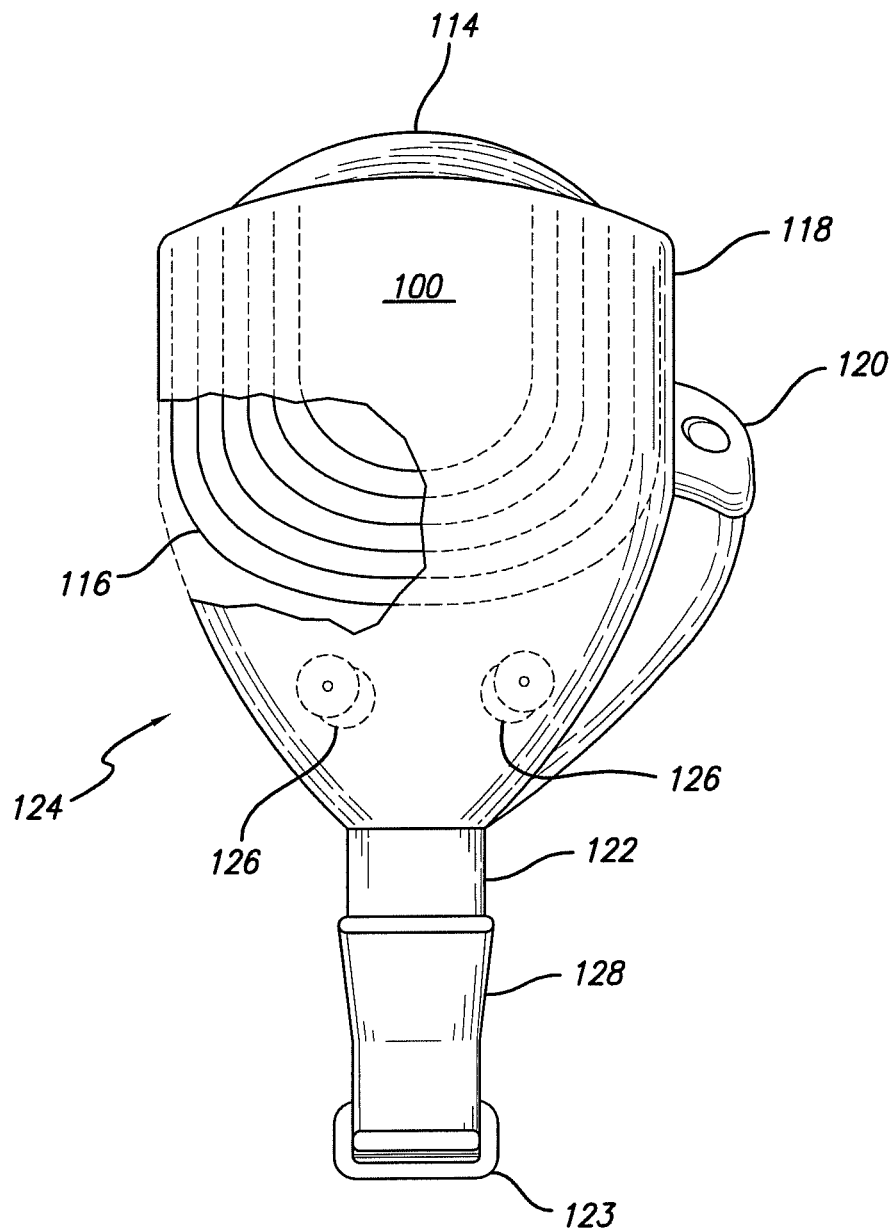
FIG. 5 is a side view of the implantable portion of a visual prosthesis showing the fan tail in more detail.

FIGS. 2 and 3 show two different perspective views of a visual prosthesis apparatus according to the present disclosure. The visual apparatus provides an implantable portion 100 and an external portion 5. Portion 5 is shown in FIGS. 2 and 3. Portion 100 is shown in FIGS. 4 and 5. The external portion 5 comprises a frame 10 holding a camera 12, an external coil 14 and a mounting system 16 for the external coil 14. The mounting system 16 also encloses the RF circuitry.

Three structural features are provided in the visual prosthesis to control the distance, and thereby reduce the distance, between the external coil 14 and the inductive (internal) coil (116, FIG. 4). The three structural features correspond to movement of the external coil along the three possible spatial axes occupied by the two coils. That is, the external and inductive coils can be viewed as being separated in anatomical axes: the medial-lateral, superior-inferior, and the anterior-posterior axis.

In this way, the first structural feature reduces the distance between the coils along the medial-lateral axis by bending the external coil 14. The distance in this medial-lateral axis should be equivalent to the separation distance of the coils if the centers of the coils are aligned. The enclosure of the external coil 14 is attached to the mounting system 16, which is attached to the leg frame 10 of the visual apparatus. While the RF circuitry within the mounting system 16 is in line with the leg frame, the external coil has been given a preferential bend 18 towards the face using a flexible connector. With the external coil 14 angled toward the face (e.g. at 25 degrees) (see FIGS. 2 and 3), the external coil 14 makes contact with the subject's face and the flexible connector allows conformation to the subject's facial contours. Thus, the external coil 14 is brought in as close as possible in the medial-lateral axis for the subject.

The second structural feature is a sliding bar mechanism controlling movement along the anterior-posterior axis. The point at which the mounting system 16 connects to the visor allows for 7 mm of adjustment along this anterior-posterior axis. The sliding bar mechanism can be fixed in place when the optimal position is found by tightening two screws on the sides of the sliding bar.

The third structural feature is adjustment of the visual apparatus along the superior-inferior axis by varying the placement of the visual apparatus along the subject's nose. When the visual apparatus is worn close to the face, the external coil 14 is higher, and when worn further from the face, the external coil 14 is lower. Using these three structural adjustments in combination, the coil separation distance can be adjusted to obtain an optimal RF link for individual subjects.

FIG. 4 shows a perspective view of an implantable portion 100 of a retinal prosthesi as disclosed. An electrode array 110 is mounted by a retinal tack or similar means to the epiretinal surface. The electrode array 110 is electrically coupled by a cable 112, which can pierce the sclera and be electrically coupled to an electronics package 114 external to the sclera. Electronic package 114 includes the RF receiver and electrode drivers.

The electronics package 114 can be electrically coupled to a secondary inductive coil 116. In one aspect, the secondary inductive coil 116 is made from wound wire. Alternatively, the secondary inductive coil may be made from a thin film polymer sandwich with wire traces deposited between layers of thin film polymer. The electronics package 114 and secondary inductive coil 116 are held together by a molded body 118. The molded body 118 may also include suture tabs 120. The molded body narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the secondary inductive coil 116 and molded body 118 are oval shaped, and in this way, a strap 122 can better support the oval shaped coil.

The entire implantable portion 100 is attached to and supported by the sclera of a subject. The eye moves constantly. The eye moves to scan a scene and also has a jitter motion to prevent image stabilization. Even though such motion is useless in the blind, it often continues long after a person has lost their sight. Thus, in one embodiment of the present disclosure, the entire implantable portion 100 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 5 shows a side view of the implantable portion of the retinal prosthesis, in particular, emphasizing the fan tail 124. When the retinal prosthesis is implanted, it is necessary to pass the strap 122 under the eye muscles to surround the sclera. The secondary inductive coil 116 and molded body 118 must also follow the strap under the lateral rectus muscle on the side of the sclera. The implantable portion 100 of the retinal prosthesis is very delicate. It is easy to tear the molded body 118 or break wires in the secondary inductive coil 116. In order to allow the molded body 118 to slide smoothly under the lateral rectus muscle, the molded body is shaped in the form of a fan tail 124 on the end opposite the electronics package 114. Element 123 shows a retention sleeve, while elements 126 and 128 show holes for surgical positioning and a ramp for surgical positioning, respectively.

In order to further understand the effects of retinal stimulation, others have applied sophisticated models for temporal processing of light stimuli in the in vitro retina. However, there are some clear distinctions between in vivo studies of implanted subjects and in vitro physiological research. In the present disclosure, the behavioral research will be studied, as opposed to electrophysiology of the in vitro retina, and study the behaviors of awake humans as opposed to an animal model. In addition, a degenerated retina and not a normal, healthy retina will be studied. For example, in RP, retinal degeneration is not simply a loss of photoreceptors. RP patients suffer a loss of other cell types as well, along with significant reorganization and possible changes in circuitry and cell function. As one might surmise, the degenerated retinal system is likely to have different temporal properties than a normal retina.

In the present disclosure, in order to determine how human visual perception depends on the timing of electrical stimulation, a temporal integration was studied during electrical stimulation. The objectives of this include: (1) determination of the potential neurophysiological elements underlying visual perception; and (2) development of a linear-nonlinear model of the temporal integration dynamics of electrical stimulation. It is of interest to understand temporal integration properties because it is thought that this information will help to generate the most effective stimulation patterns. The first step is to look at how visual perception depends on the timing of electrical stimulation patterns.

Figure 6:
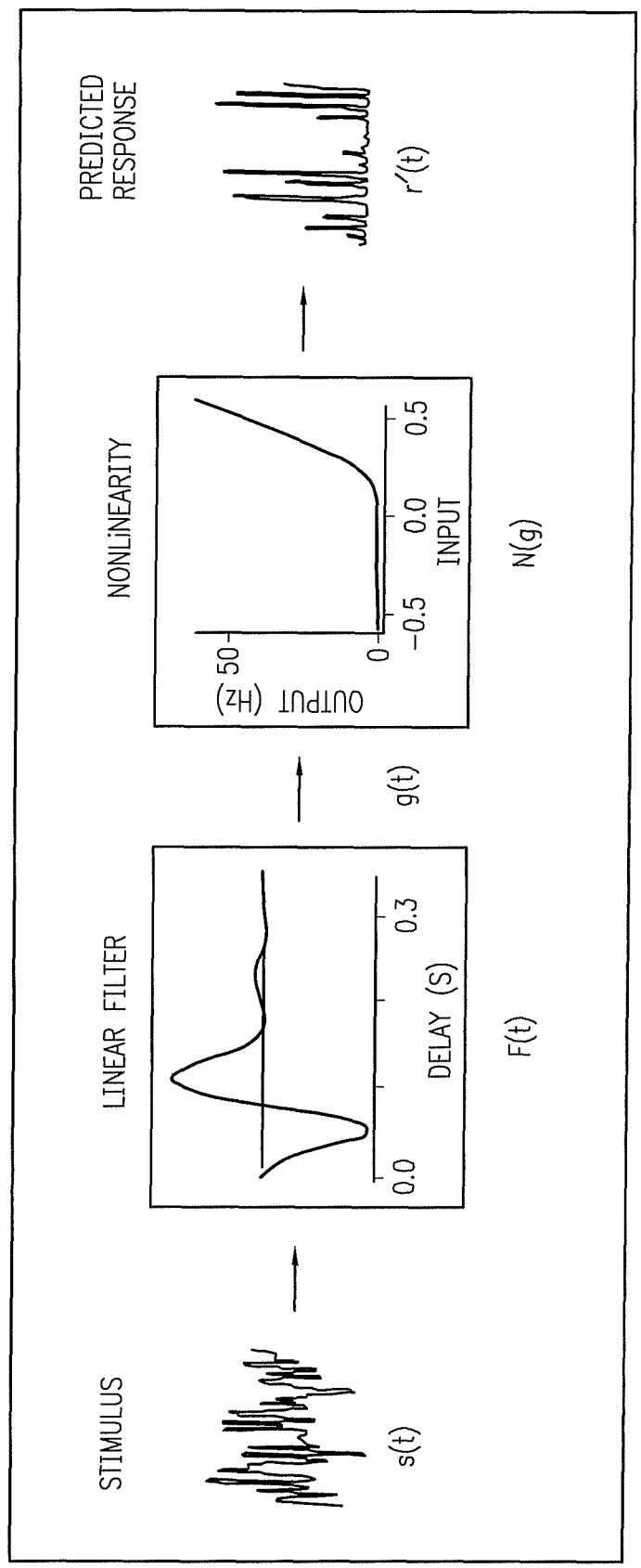
FIG. 6 is a graph showing linear-nonlinear models can predict retinal firing to light stimuli.

FIG. 6 shows a graph of how linear-nonlinear models can predict retinal firing to light stimuli. As noted above, there are models in the art that evaluate the early visual system's response to light stimuli. One example is a model of temporal contrast adaptation in retinal ganglion cells, where the resulting spike train can be predicted based solely upon the light stimulation input (Chander, D. and E. J. Chichilnisky (2001), *Journal of Neuroscience* 21(24): 9904-16; Kim, K. J. and F. Rieke (2001), J *Neuroscience* 21(1): 287-99; Baccus, S. A. and M. Meister (2002), *Neuron* 36(5): 909-19.)

The linear/nonlinear model aides in the prediction of ganglion cell responses to light stimuli, wherein a light flicker stimulus is convolved with a linear filter with a particular time constant. The output of this convolution is then passed through an expanding nonlinearity to ultimately predict the neural response. To evaluate whether such a model is able to predict the perceptual response to electrical stimulation, and how the temporal properties differ when using electrical stimulation rather than light stimulation, perceptual threshold is observed as a function of pulse width.

Figure 7:
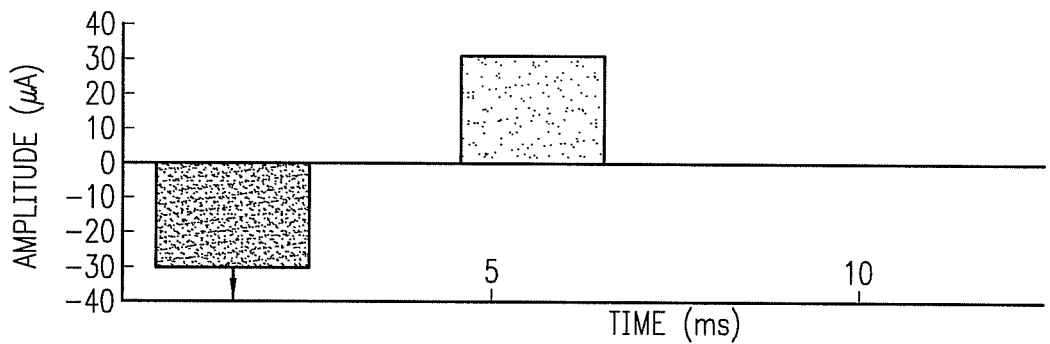
FIG. 7 is a graph showing the effect of pulse duration.

FIG. 7 shows a graph of a biphasic pulse. In accordance with FIG. 7, the stimuli are single, biphasic, cathodic-first, charge-balanced pulses, wherein the pulse width varied between 0.075 milliseconds (ms) and 4 ms, per phase. Anodic pulses are approximately fifty percent as effective as cathodic pulses, thus the anodic pulses are not necessary to consider (Jensen, R. J., O. R. Ziv, et al. (2005), *Invest Ophthalmol Vis Sci* 46(4): 1486-96).

Furthermore, the anodic pulses are considered to be far less effective at driving a response in the in vitro retina. This is the result of the orientation of the stimulating electrode relative to the ganglion cell. In this configuration, the negatively-charged cathodic pulse 'pulls' the positive cations within the cell towards the axon hillock, where there is the highest concentration of voltage-gated channels. Therefore, for the method according to the present disclosure, the anodic phase should not be considered when it comes to evaluating the biphasic pulse and its influence on perception.

Figure 8:
FIG. 8 is a graph showing a method for determining visual perceptual threshold.
Figure 8:
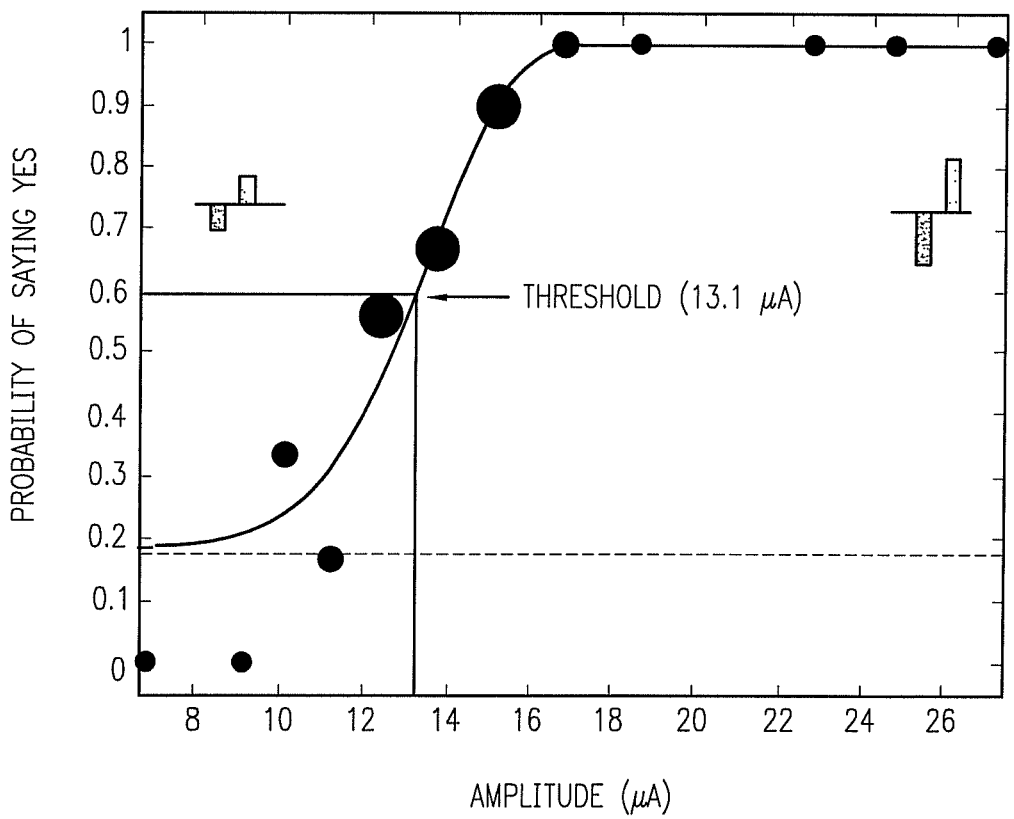

FIG. 8 shows a graph of a method for determining visual perceptual threshold, wherein the threshold was determined as follows. Subjects were exposed to a series of stimuli using a yes-no paradigm wherein half the trials contained no stimulus. The subjects reported whether the trial contained a stimulus or not. The current amplitude was varied using a 3 up, 1 down staircase. In other words, if the subjects got 3 correct answers in a row the subsequent current signal was made more difficult by decreasing the current a step. Likewise, if the subject answered incorrectly, the subsequent current signal was made easier by increasing the current by one step. Thresholds were measured on single electrodes using a single interval, yes-no procedure. On each trial, subjects were asked to judge whether or not each trial contained a stimulus. This reporting procedure meant that subjects were likely to report stimulation for either a light or dark spot; subjects were explicitly instructed to include either type of percept in making their decision. Half of the trials were stimulus-absent catch trials. During each staircase, only amplitude varied. All other parameters (frequency, pulse width, pulse train duration, and the number of pulses) were held constant. Each threshold was based on a minimum of 125 trials and error bars were estimated using Monte-Carlo simulation (Wichmann and Hill, 2001).

The curve shown in FIG. 8 is an example of a generated psychometric function, which was used to analyze the behavioral data. The x-axis is the current amplitude and the y-axis is the probability that the subject saw the stimulus, 1 being that the subject saw it every time at that particular current. The black dots are the subject/patient responses for a specific stimulus condition (a specific current amplitude), with the larger dots representing a greater number of trials at that condition. As is shown in FIG. 8, there is a dramatic shift in performance between 10 uA and 16 uA. After adjusting the curve to the false alarm rate, the curve was fit with a Weibull function and the 50% point was the determined threshold. The Weibull function allows for many different distributions. This function is a common cumulative distribution that is frequently used for life data because its slope parameter can be adjusted to allow the curve to represent different distributions.

Figure 9:
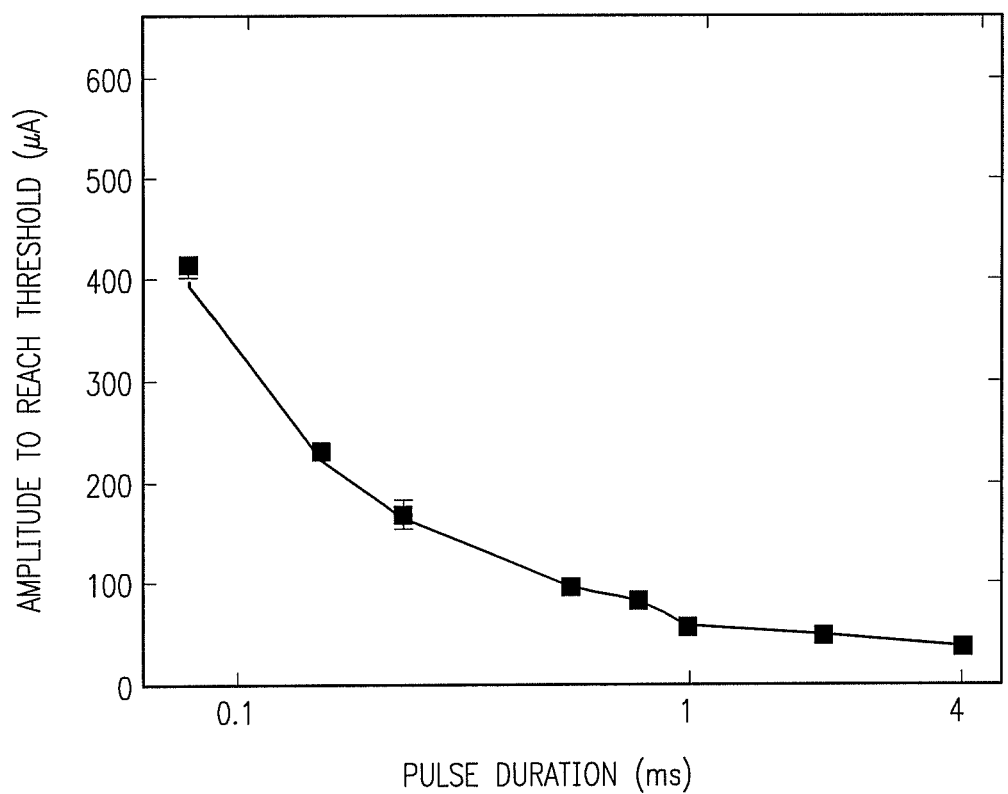
FIG. 9 is a graph showing threshold as a function of pulse width.

FIG. 9 is graph showing threshold as a function of pulse duration or width. FIG. 9 is an example curve (typical of data from 10 electrodes, 2 subjects). Data can be modeled using a simple leaky integrator model. A leaky integrator model represents the accumulation and dissipation of some input (e.g. electric current or charge) that accumulates and dissipates with a specific rate that depends on the value of the time constant. Across all data in FIG. 9, time constants of <1 ms are found, which is consistent with chronaxie values for ganglion cell integration periods (Jensen et al., 2005). The pulse width is on the x-axis varying between 0.075 ms and 4 ms, and the y-axis is the amplitude to reach threshold. The eight boxes shown in the figure represent measured thresholds at their corresponding pulse widths. So, for example, at 0.075 ms, it requires approximately 425 microAmperes ($\mu A$) of current for the patient to be able to see that stimulus 79% of the time. The data show that as the pulse width is increased, there is a decrease in current amplitude needed to reach the threshold. The black line, represents the current model and the fit estimation of this particular data set. Additionally, this data can be fit using a simple leaky integrator model (Kandel, E. R., J. H. Schwartz, et al. (1991). Principles of Neural Science. Norwalk, Conn., Appleton & Lange) having a single free parameter (tau or time constant) that represents the integrative behavior of the system.

Figure 10C:
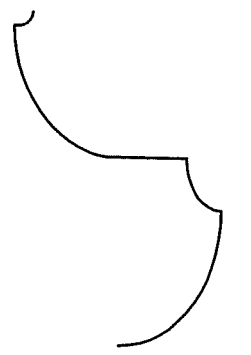
FIGS. 10A-10C are graphs showing the varying integration rates of different cell types.
Figure 10B:
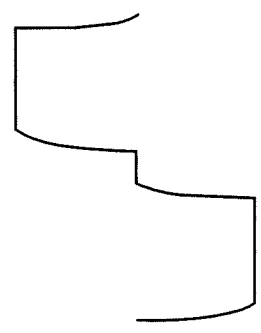
Figure 10A:
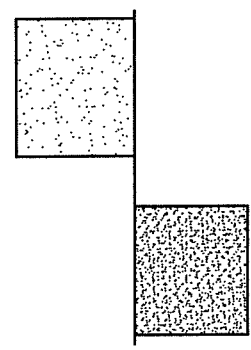

FIGS. 10A-10C show that different cell types integrate charge at different rates with cathodic phases in grey and anodic phases in black. FIG. 10 also shows how a leaky integrator model would integrate a biphasic pulse (FIG. 10A) using a short (FIG. 10B) and long (FIG. 10C) time constant. FIG. 10A represents an input stimulation pattern (biphasic pulse). FIG. 10B represents a fast integrator response to the input, typical of ganglion cells. FIG. 10C represents a slow integrator response, typical of bipolar cells.

For further example, one can imagine two different biphasic pulses that differ in their pulse width, where one is relatively long and the other is short. If a leaky integrator model is applied with fast temporal properties, the response curve follows the shape of the input reasonably well. On the other hand, if the model integrates more slowly, the response is more sluggish, as represented in FIG. 10C by the shallower slope of the response curve. In fact, if the biphasic pulse is short, the amplitude of the response curve is greatly diminished. Applying this concept to the physiology of Jensen (Jensen et al., 2005) and Fried (Fried, S. I., H. A. Hsueh, et al. (2006), *J Neurophysiol* 95(2): 970-8.) who reported that integration periods of ganglion cells are substantially faster than those of either bipolar or amacrine cells, suggests that it may be possible to exclusively activate ganglion cells with shorter pulse widths.

Figure 11:
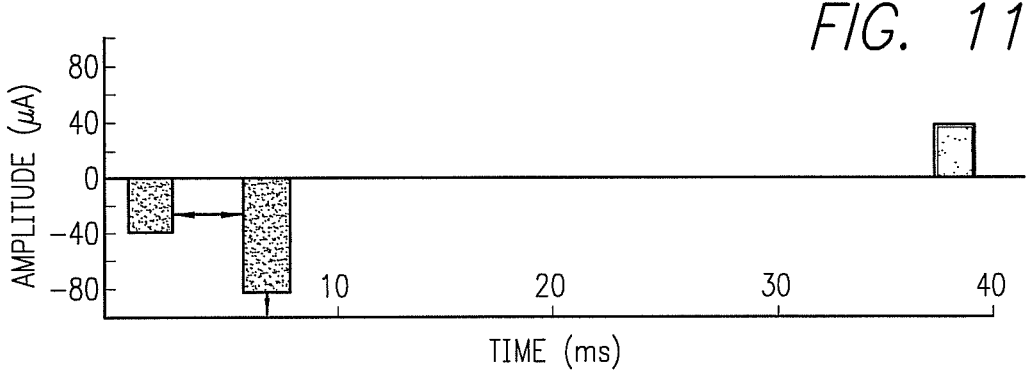
FIG. 11 is a graph showing summation across pulse pairs.

Another approach to evaluating the temporal integration of the system is by looking at how two separate pulses sum in time. FIG. 11 is a graph showing summation across pulse pairs. Stimuli were 0.075 ms pseudo-monophasic cathodic pulses. The first pulse had fixed current amplitude (sub-threshold). The second pulse followed with a variable delay (0.15-12 ms). The experiment, illustrated by FIG. 11, evaluates the summation across pulse pairs. In other words, the experiment determines how the first pulse, (i.e. the conditioning pulse) contributes to the threshold response of the second pulse, (i.e. the test pulse). The stimuli were pseudo-monophasic because, for obvious safety reasons, a charge-balanced anodic phase is included, as shown by the positive pulse to the right of FIG. 11. The difference here is that the anodic pulses were presented later in time by about 30 ms.

Figure 12:
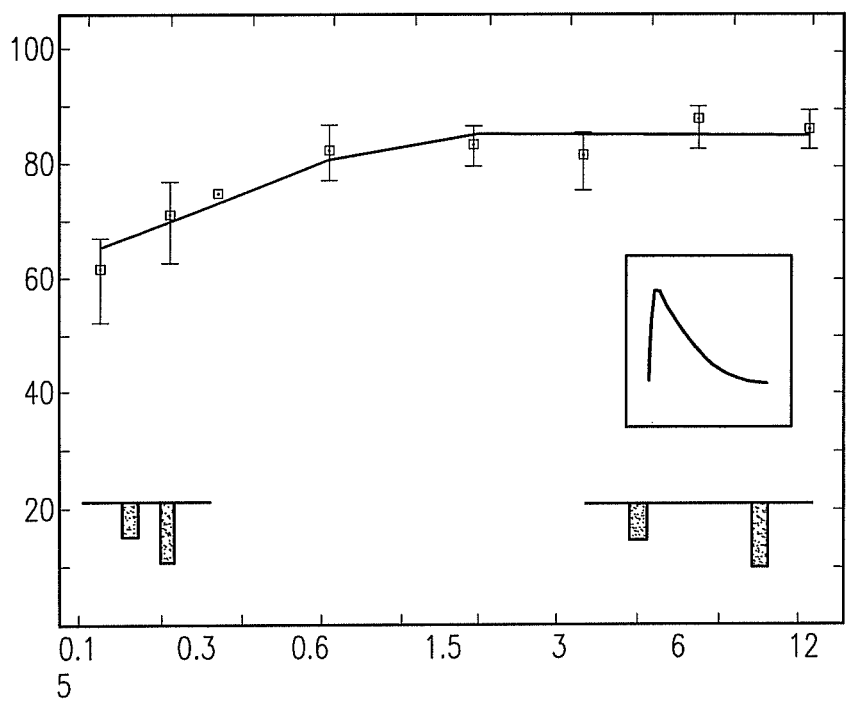
FIG. 12 is a graph showing threshold for pulse pairs.

FIG. 12 is a graph showing threshold for pulse pairs. The graph derives from a data set of 8 different electrodes across two subjects. The time constants were the same (<1 ms) as the single pulse data are consistent with ganglion cell stimulation. With pulse pair summation it was determined that there is a critical window of integration.

In particular, the x-axis of FIG. 12 shows the delay between pulse pairs, and the y-axis is the amplitude to reach threshold. The critical window of integration was observed to be somewhere short of one millisecond. More specifically, looking at the portion of the curve before the 1 ms delay value, a short increase in delay provides a large increase in amplitude to reach threshold. On the other hand, after the one millisecond point, the curve asymptotes and the current value at which it asymptotes is the same as that for a single biphasic pulse. This observation means the following: first, that the secondary anodic phase has no influence on threshold, and secondly, that the integration period is very short. If these data were fitted to a leaky integrator model, time constants would be similar to those of ganglion cells.

Therefore, all the data shown thus far provide a strong indication of how simple and very short stimuli are integrated over time. However, a further objective of the present disclosure is to determine continuous stimulation in order to provide visual information to improve navigation and visual recognition. In view of this further objective, one or two electrical pulses are not enough.

Figure 13:
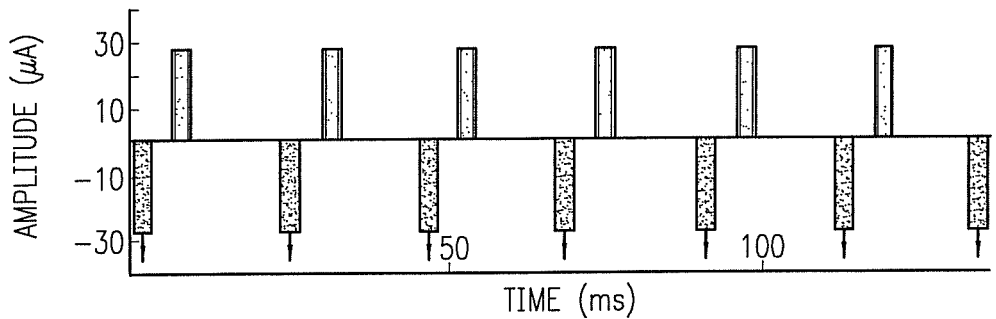
FIG. 13 is a graph showing fixed duration pulse trains.

FIG. 13 is a graph showing a fixed duration pulse train, i.e. a series of multiple pulses where every pulse has the same width. In particular, in order to determine how multiple pulses integrate over time, stimuli were fixed duration pulse trains of 200 milliseconds. Pulses were either 0.975 or 0.075 milliseconds in duration, and frequency varied between 5 Hz and 225 Hz. Amplitude of all pulses in the train varied simultaneously to find threshold. In other words, the amplitude of each pulse within the pulse train increased and/or decreased at the same time.

Figure 14:
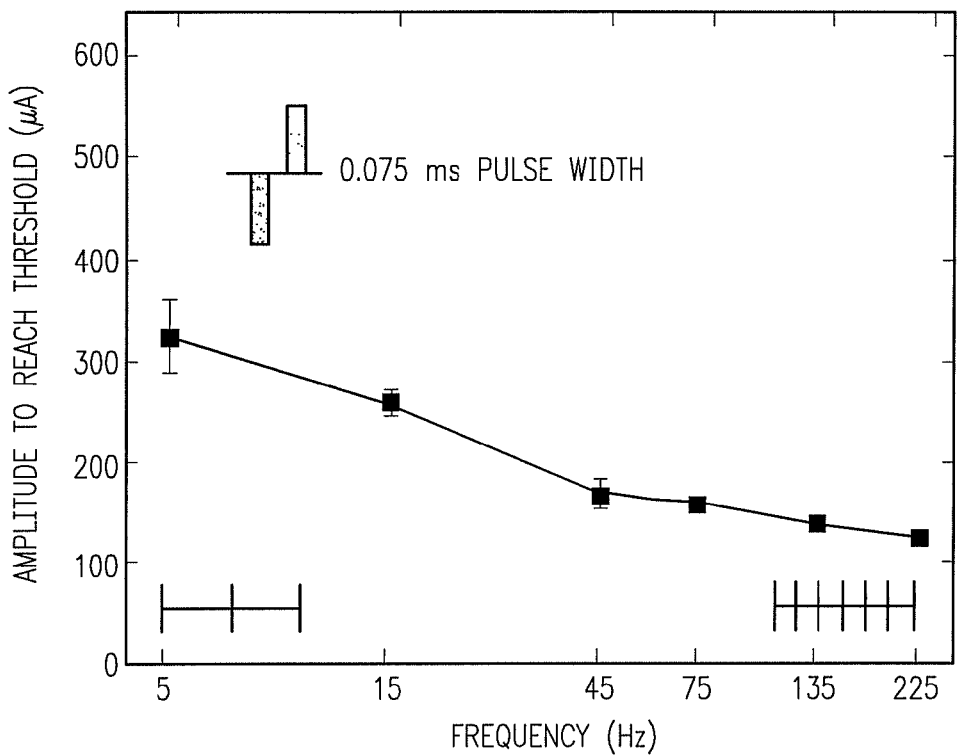
FIG. 14 is a graph showing threshold for fixed duration pulse trains of 0.075 ms pulse width.
Figure 15:
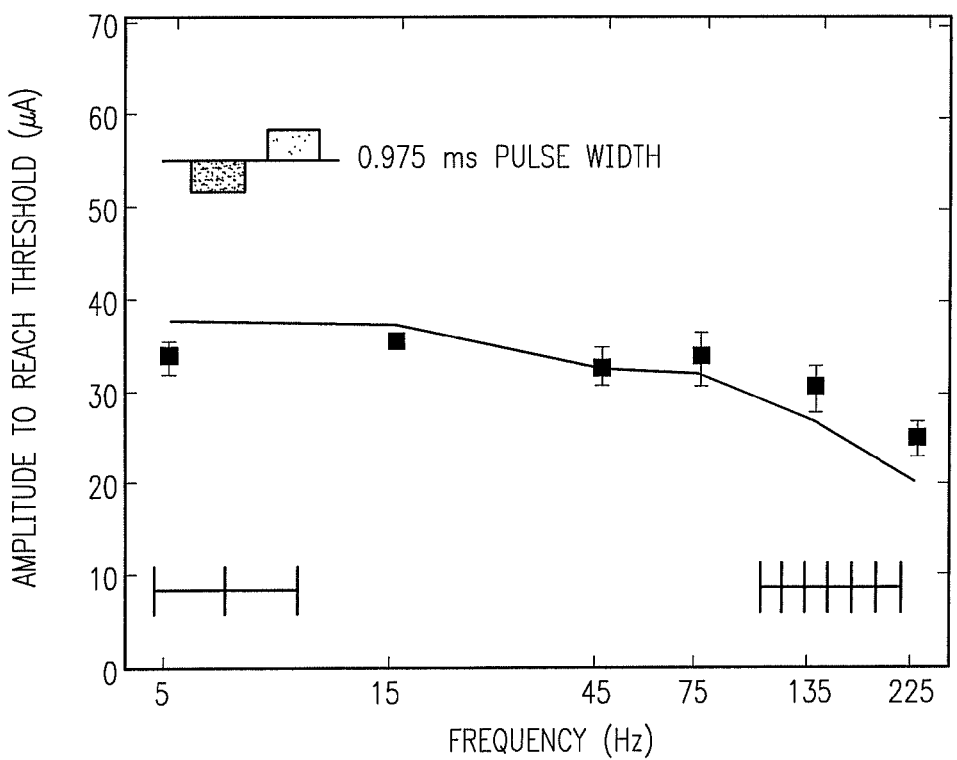
FIG. 15 is a graph showing threshold for fixed duration pulse trains of 0.0975 ms pulse width.

FIGS. 14 and 15 show graphs indicative of threshold for fixed duration pulse trains like the one shown in FIG. 9.

It has already been discussed above that the reduction in the amount of current needed to reach the threshold is due to interactions between pulses. FIG. 14 and FIG. 15 show that the decrease in threshold is driven by the frequency of the pulses.

The graph of FIG. 14 refers to data coming from pulse trains having widths (duration of each pulse) of 0.075 ms. On the other hand, the graph of FIG. 11 refers to data coming from pulse trains having widths of 0.975 ms. In both cases, the x-axis frequency range is the same, i.e. 5 Hz to 225 Hz. However, there is a significant difference between the amplitude values to reach threshold of the two Figures. The values of FIG. 14 (between about 300 and about 100 microAmperes) are an order of magnitude greater than the values of FIG. 15 (between about 40 and about 20 microAmperes). In both graphs, solid lines have been added to show the behavior of the model.

The reason for the different result is the difference in pulse width (0.075 ms vs. 0.975 ms). In particular, as the pulse width is increased, less current is required to drive the system to threshold, as also previously discussed.

Therefore, it appears that a decrease in threshold is a function of frequency of the pulses. However, the response to pulse trains is dynamic, and the resulting pulse train data cannot be fitted to a leaky integrator model, as there are interactions between pulses that go beyond that of the model. Also, there is one potential confound with the pulse train data, and that is that since fixed duration pulse trains are being used, in order to change the frequency an increase in the number of pulses is required. For example, at 15 Hz, 3 pulses are used, and at 225 Hz, 45 pulses are used.

In order to determine if a decrease in threshold is a function of frequency or a function of the number of pulses, or a function of both, the applicants have examined the relationship between frequency and the number of pulses.

Figure 16A:
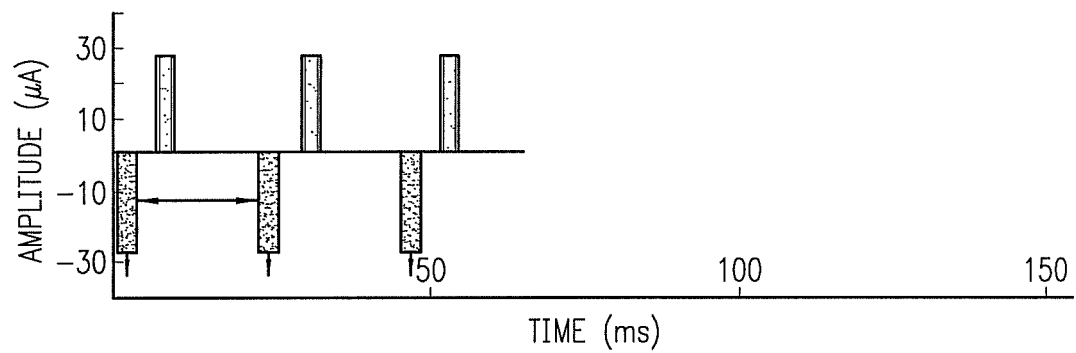
FIGS. 16A, 16B are graphs showing threshold for variable duration pulse trains.
Figure 16B:
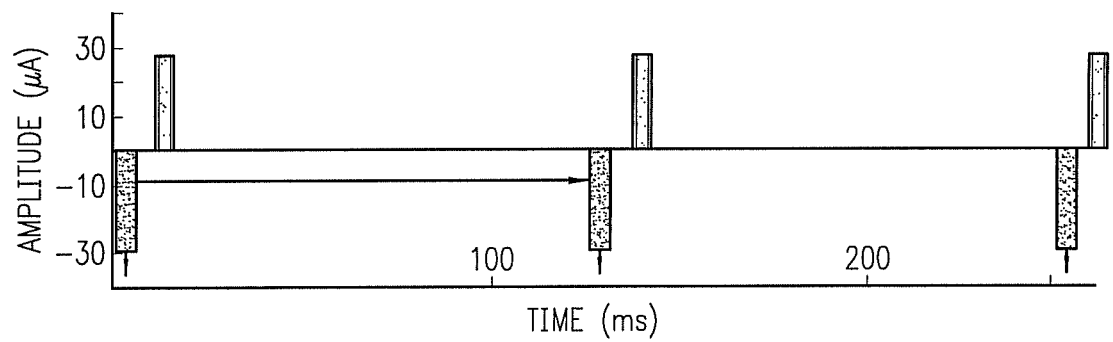

FIGS. 16A and 16B are graphs showing threshold values for variable duration pulse trains. In this example, the stimuli consisted of pulse trains of 2, 3, and 15 pulses (where the 2 and 3 pulses examples are shown in FIG. 12). The frequency of these pulse trains was varied by changing the delay between the biphasic pulses. The delay varied from 0.075 ms to 300 ms, corresponding to a range of frequencies between approximately 3000 and approximately 3 Hz. As with the fixed duration pulse train data, perceptual threshold was measured by varying the amplitude of all the pulses within the pulse train simultaneously. In other words, the amplitude of each pulse within the pulse train increased and/or decreased at the same time.

Figure 17:
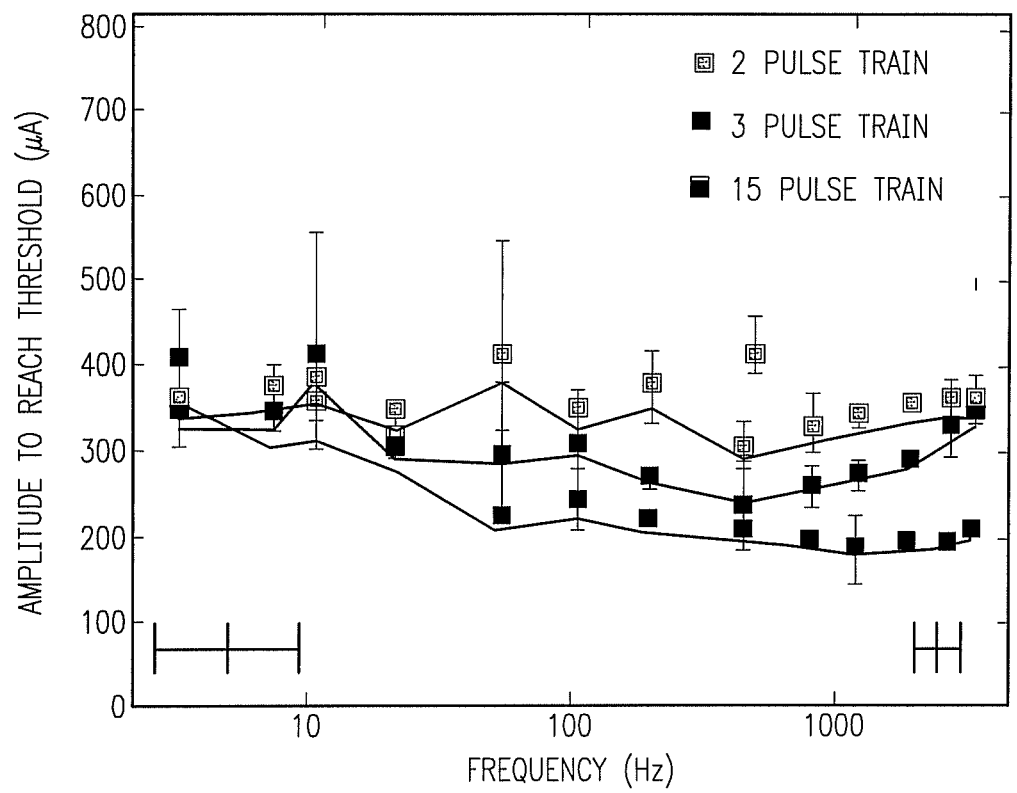
FIG. 17 is a graph showing the relationship between threshold, frequency and the number of pulses.

FIG. 17 is a frequency vs. amplitude-to-reach-threshold graph similar to the ones shown in FIGS. 10 and 11, where relationship between frequency and number of pulses is also shown. Here, the x-axis is represented in a logarithmic scale. Three curves are shown. The curve on top corresponds to a 2 pulse train. The curve in the middle corresponds to a 3 pulse train. The curve on the bottom corresponds to a 15 pulse train. Differences in behavior between the different numbered pulse trains do not appear until frequencies above about 20 Hz (about 50 Hz), wherein as the number of pulses is increased, there is a decrease in necessary current to reach threshold The three curves are separated by 300 ms at the lowest frequency (3 Hz) and by 0.075 ms at the highest frequency (3333 Hz). It should be noted that these curves, as with all the data presented, are generated using a Monte Carlo simulation.

The data of FIG. 17 show that there is no statistical difference in perceptual threshold for all three of the different numbered pulse trains. That is, presenting two pulses at 20 Hz or presenting fifteen pulses at 20 Hz results in the same perceptual threshold, and therefore, perceptual threshold becomes independent on pulse timing. This is more clearly represented when the data in the fifteen pulse trains is averaged over six electrodes for two patients. Looking at the higher frequencies, there is no statistical change in threshold as a function of frequency, representing independence on timing but a dependence on pulse number. The lower frequencies, as noted above, are independent of pulse number, but have a clear relationship to pulse timing.

Figure 18:
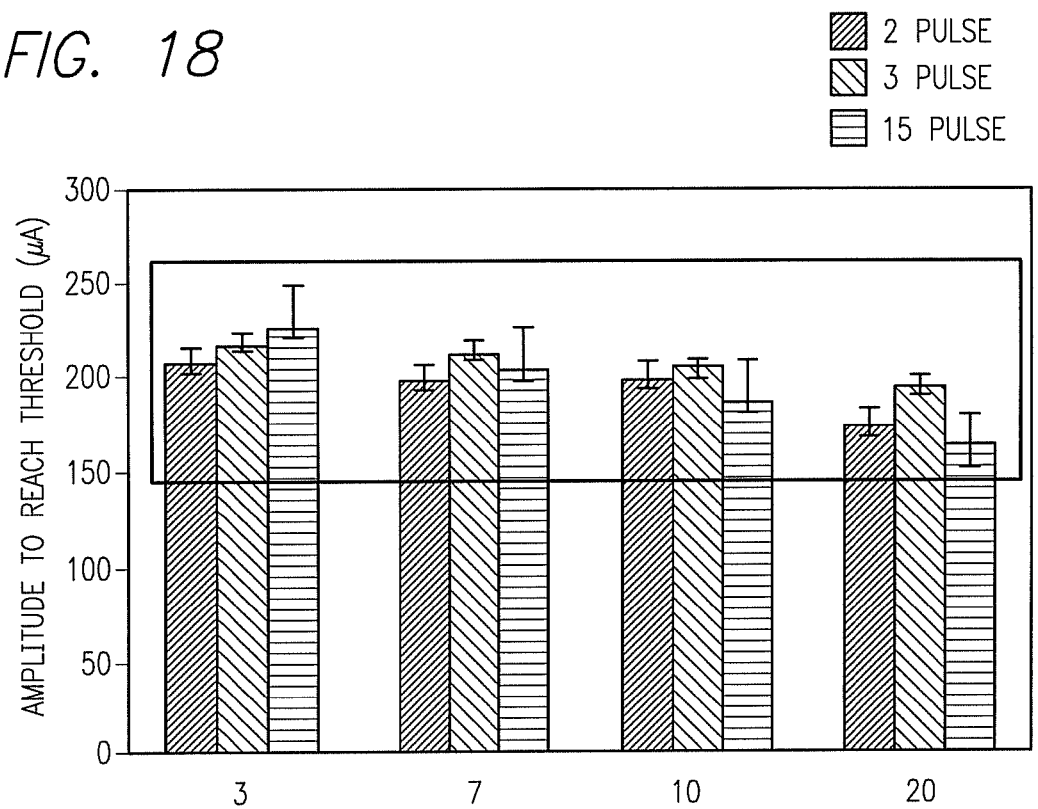
FIG. 18 is a graph showing that the thresholds of pulse trains with frequency below 50 Hz are independent of pulse number.

FIG. 18 is a graph showing that thresholds for pulse trains with frequencies below about 50 Hz are independent of the number of pulses. The graph refers to data for thresholds for the two (grey bar), three (diagonal-lined bar) and fifteen (horizontal-lined bar) pulse train data of FIG. 17, averaged over six electrodes and over two subjects, plotted for frequencies of 3, 7, 10 and 20 Hz, wherein the error bars represent the standard error. Although there may be slight statistical differences between these data, and there is a trend downward as a function of frequency for the fifteen pulse data, the statistical differences between the two, three, and fifteen pulse data, when compared at each frequency, are very similar. This similarity between pulse trains suggests that perceptual thresholds of the input are independent of pulse number. However, for the fifteen pulse data, a dependency on pulse timing occurs at lower frequencies.

Figure 19:
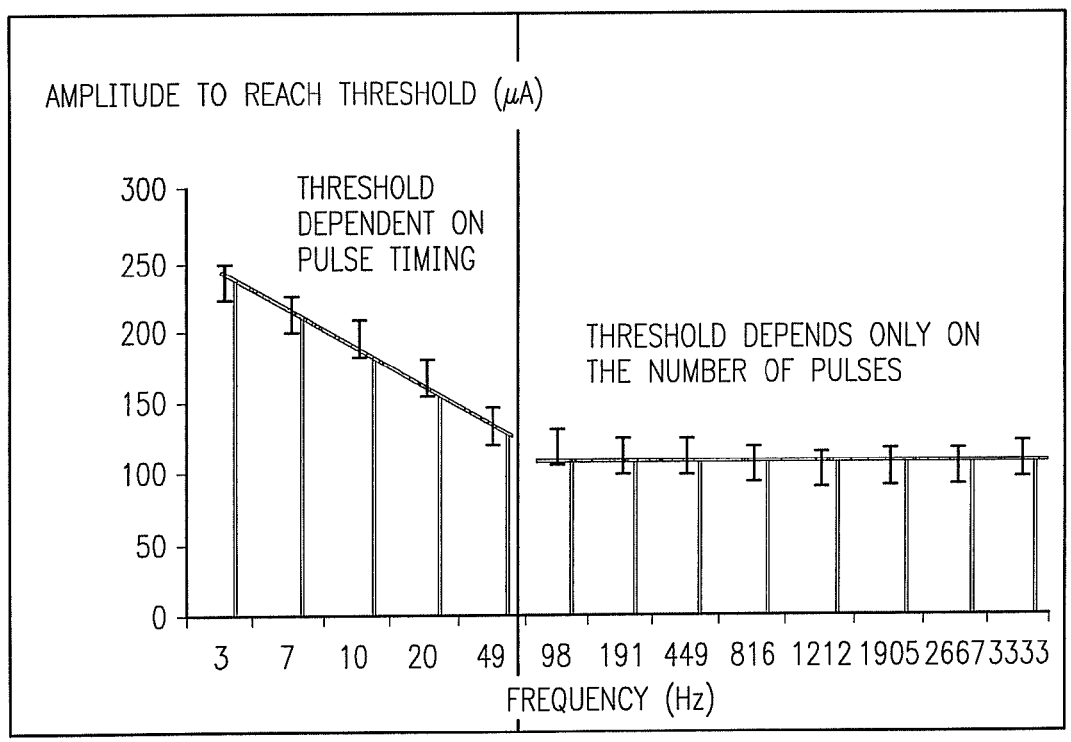
FIG. 19 is a graph showing that thresholds for pulse trains with frequencies above 50 Hz are independent of pulse timing.

In view of the data in FIG. 19, and the disclosure that ganglion cells operate in a range that is somewhere below 250 Hz (O'Brien, B. J., T. Isayama, et al. (2002), *Journal of Physiology* 538(Pt 3): 787-802), it is determined that increasing frequencies above this operating ceiling does not supply the system with any additional information about the stimulus because ganglion cells are computationally incapable of processing frequencies in this higher range. In another aspect, if the cortex is thought of as a low pass filter, all the pulses within these higher frequency trains fall within the limits of this integrative window. Thus, if the window of integration of the cortex is on the order of several hundred milliseconds, as long as all the pulses within that train fall within that window (above ~50 Hz), the response will be the same.

Figure 20:
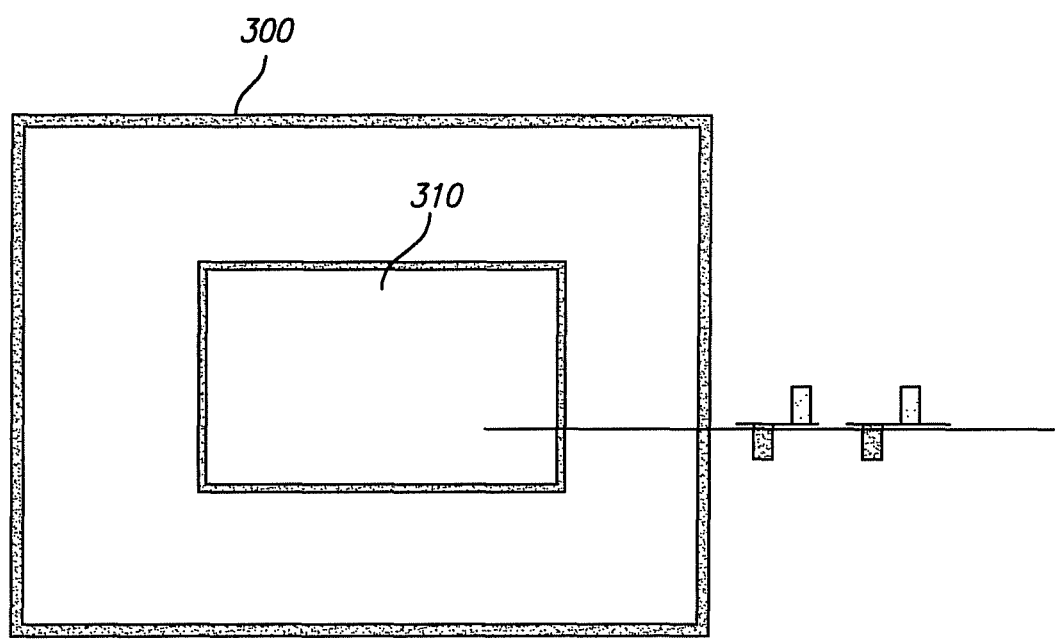
FIG. 20 is a schematic of a retinal stimulation device comprising a stimulation pattern generator.

FIG. 20 shows a stimulation pattern generator 310 which can provide the impulsive electrical signals to implement a determined stimulation pattern from observing a perceived threshold. This stimulation pattern generator can be programmed to provide a pattern of pulse trains having a pulse train frequency and a pulse width. For example, the stimulation pattern generator can be programmed to provide a pulse train having a frequency less than 50 Hz, wherein the pulse width is fixed at 0.075 ms or 0.975 ms. Alternatively the stimulation pattern generator can provide a pulse train having a frequency higher than 50 Hz, wherein the pulse width is variable. As shown, the stimulation pattern generator is connected to a retinal stimulating device 300. An example of a retinal stimulating device is shown in FIGS. 1 and 2.

Suprathreshold brightness-matching was carried out on single electrodes using a two-interval, forced-choice procedure. Each trial contained two intervals with each interval containing a pulse train of a different frequency. For example, interval 1 might contain a 15 Hz pulse train and interval 2 might contain a 45 Hz pulse train. Subjects were asked to report which interval contained the brighter stimulus. A one-up, one-down staircase method was used to adjust the amplitude of the higher frequency pulse train based on the observer's response. The first brightness match was made by fixing the amplitude of a "standard" 5 Hz pulse train (a single pulse within a 200 ms window) to be 2 or 3 times threshold amplitude, and finding the amplitude needed for a 15 Hz "test" pulse train to match the brightness of the standard pulse train. The 15 Hz pulse train then became the "standard" pulse train and was compared in brightness to a 45 Hz "test" pulse train and so on. Each brightness match was based on a minimum of 80 trials and error bars were again estimated using an adaptive sampling Monte-Carlo simulation (Wichmann and Hill, 2001). Using this method, we were able to obtain an iso-brightness curve that represented the current amplitude needed to maintain the same subjective brightness across a wide range of frequencies.

In each of our two subjects, we measured detection thresholds for 10 different categories of stimulation pattern (FIGS. 21A-G, 24A-C) and suprathreshold perceived brightness for 6 different categories of stimulation pattern (FIG. 22A-C, 25A-C). Data were collected from 12 electrodes across the two subjects. Across these 12 electrodes, we collected 534 threshold and 116 suprathreshold measurements in total. Patients typically reported that phosphenes appeared white or yellow in color, and round or oval in shape. At suprathreshold, percepts were reported as brighter and the shape occasionally became more complex than a simple round or oval shape. The shapes were reported as being approximately 0.5-2 inches in diameter at arm's length, corresponding to roughly 1-3 degrees of visual angle. Occasionally, a dark spot rather than a white or yellow percept was reported. In this case, the patient would use the relative contrast of the spot for detection (threshold) or 'brightness comparison' (suprathreshold).

Data were modeled using a linear-nonlinear model (FIG. 23) similar to models of auditory stimulation in cochlear implant users (Shannon, 1989), retinal ganglion cell spiking behavior during temporal contrast adaptation (Chander and Chichilnisky, 2001; Rieke, 2001; Baccus and Meister, 2002), and models of human psychophysical temporal sensitivity (Watson, 1986). Here we simply present the components of the model; a more detailed explanation of each stage of the model is described below. We began by convolving the stimulus with a temporal low-pass filter, or "leaky integrator" using a 1-stage gamma function as its impulse response:

$$r_1(t) = f(t) * \delta(t, 1, \tau_1) \quad (1)$$

where f(t) is the electrical stimulation input pattern, t is time (ms), and $\delta$ is the impulse response function with time constant $\tau_1$. (We report here time constants ($\tau$) rather than chronaxie values (c), which are also commonly reported in the literature: $\tau = c/\ln(2)$). The gamma function used to model the impulse response can be generally described as:

$$\delta(t, n, \tau) = \frac{e^{-t/\tau_1}}{\tau(n-1)!}(t/\tau)^{n-1}, \quad (2)$$

where t=time, n=the number of identical, cascading stages, and $\tau$ is the time constant of the filter (the 1-stage gamma function in Eq. 1 is simply an exponential function.)

We assumed that the system became less sensitive as a function of accumulated charge. This was computationally implemented by calculating the amount of accumulated cathodic charge at each point of time in the stimulus, c(t), and convolving this accumulation with a second 1-stage gamma function having a time constant $\tau_2$. The output of this convolution was scaled by a factor $\epsilon$, and then subtracted from $r_1$ (Eq. 1), $$r_2(t) = r_1(t) - \epsilon(c(t) * \delta(t, 1, \tau_2)). \quad (3)$$

$r_2$ was then passed through an expansive nonlinearity, $$r_3(t) = (r_2(t))^\beta \quad (4)$$

and convolved with a low-pass filter described as a 3-stage gamma function with time constant $\tau_3$, $$r_4(t) = r_3 * \delta(t, 3, \tau_3). \quad (5)$$

We assumed that the response reached threshold (or the point of equibrightness during suprathreshold experiments) when $$\max_t(r_4) >= \theta \quad (6)$$

where $\theta$ is a fixed constant.

Optimization was carried out using a subset of the full set of data—2 electrodes for each of the two patients (S05-B3 & C2, S06-B1 & C2).

The parameter values $\tau_1$, $\tau_2$ and $\tau_3$ were optimized across the 7 threshold and 3 suprathreshold experiments using a standard least-squared error minimization technique. The parameters $\epsilon$ (linear shift as a function of charge) and $\beta$ (power nonlinearity) were fit separately for threshold and suprathreshold levels of stimulation. When fitting suprathreshold data, $\epsilon$ and $\beta$ were allowed to vary across different levels of apparent brightness.

The parameter that represented the model output at threshold, $\theta$, was allowed to vary across each experiment on a given electrode. Variation in $\theta$ accounts for differences in mean sensitivity between the two patients, differences in sensitivity across electrodes, and slight changes in electrode sensitivity over time. The set of data in this paper were collected over slightly more than a two year period, during which we observed gradual changes in sensitivity over time which appeared to be mainly due to slight changes in the position of the electrode array over time. Because each experiment on a given electrode was collected over a relatively short time period (usually within a week or two) we assumed that electrode sensitivity did not vary within an experiment.

After optimizing the model using a subset of the full set of data, we averaged the best-fitting parameters values for $\tau_1$, $\tau_2$, $\tau_3$, $\epsilon$ and $\beta$ across all the four electrodes used for optimization and used these mean values to predict threshold and suprathreshold data for novel electrodes. For these novel electrodes the only parameter allowed to vary across each experiment was the threshold parameter, $\theta$.

Figure 21E:
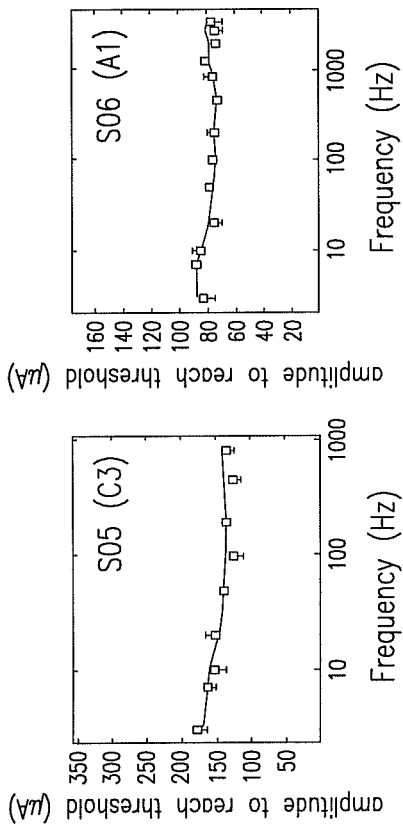
Figure 21E:
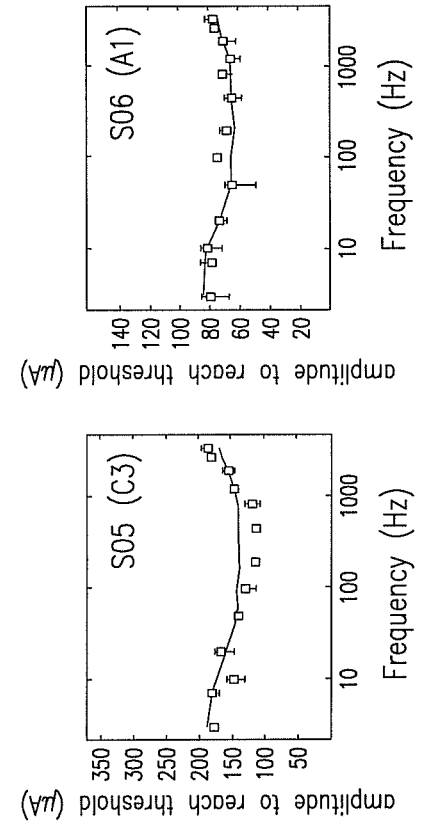
Figure 21E:
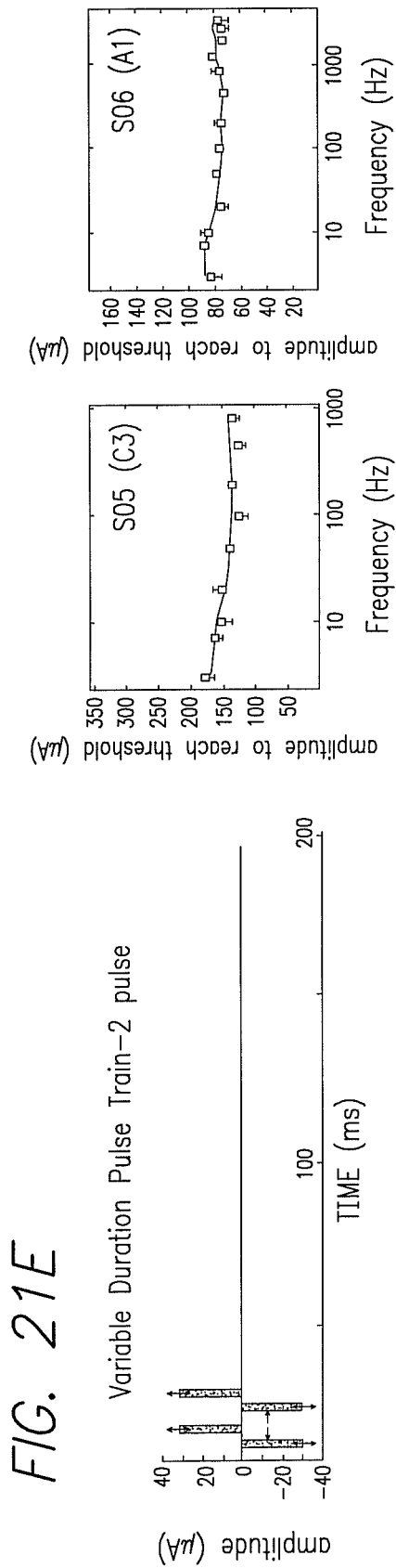
Figure 21F:
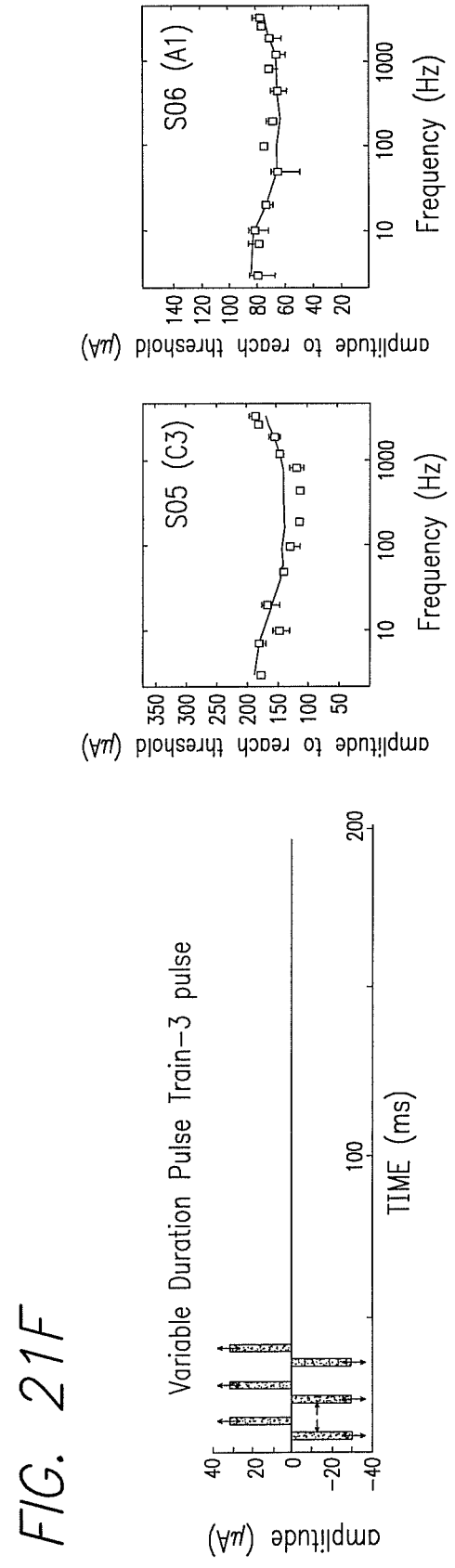
Figure 22B:
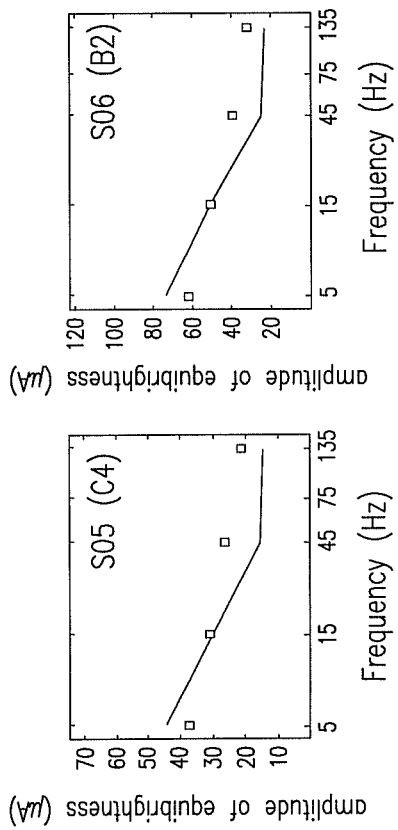
FIG. 22 A-C is a series of bar charts and response graphs for suprathreshold stimulation where each row contains an example of the pulse train stimulus and data with model predictions from the constrained model.
Figure 22B:
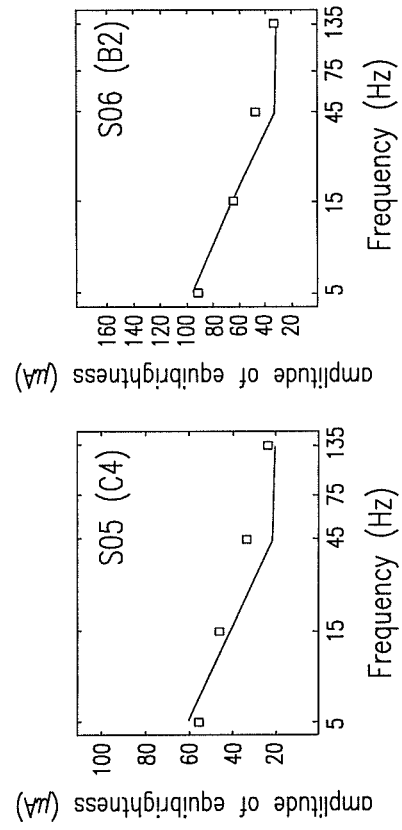
Figure 22B:
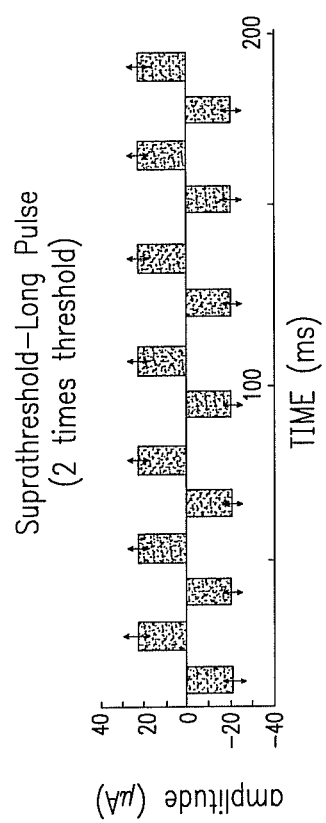
Figure 22C:
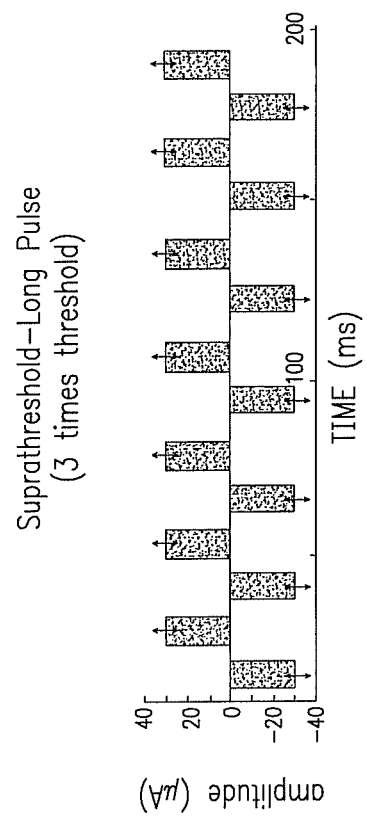

The solid lines in FIGS. 21A-G show model predictions to threshold data for a single novel electrode for each of the two patients (S05-C3, S06-A1). The solid curves in FIGS. 22A-C show suprathreshold model predictions for a single novel electrode for each of the two patients (S05-C4, S06-B2). The model and parameter values generalized to successfully predict data on novel electrodes.

We then examined the ability of the model to predict responses to novel pulse train waveforms not used to optimize model parameters. We again used fixed values for $\tau_1$, $\tau_2$, $\tau_3$, $\epsilon$ and $\beta$ based on the electrodes and stimulus patterns used for optimization, and the only parameter allowed to vary across each experiment was the threshold parameter, $\theta$.

The novel waveforms consisted of repeated bursts of 3 pulses with a variable inter-burst delay. Data for this novel waveform was collected at both threshold and suprathreshold levels of stimulation on novel electrodes not used for the original model fits (S05-A1, S06-A2). Results are shown in FIGS. 24 and 25, respectively. The model and parameter values generalized to successfully predict these data from a novel stimulation pattern on a novel electrode.

Our model, like those describing the perception of light stimuli, presumably approximates the responses of neuronal populations. In the case of our threshold experiments, it is possible that firing within a relatively small number of retinal cells mediated detection. Electrical stimulation thresholds for single pulses (FIG. 21A) are comparable to those reported in the animal in vitro electrophysiological literature. This is surprising, given that the definition of threshold routinely within these in vitro studies is the current that reliably elicits at least one spike in a single cell. However it has been previously shown that subjects with normal vision can reliably detect a single photon of light (Hecht et al., 1942), suggesting that a very small increase over the baseline firing rate of ganglion cells is probably sufficient to mediate behavioral detection. Thus, thresholds in our subjects may have been mediated by a relatively small number of spikes: these spikes might, of course occur either in a single cell or across several cells. At suprathreshold our model presumably approximates the population response of a larger number of cells each producing one or multiple spikes.

We now provide detailed description of each component and parameter of the model.

$\tau_1$ (Eq. 1). The parameter $\tau_1$ represents the time course of the first stage of current integration. The value was mainly constrained by the shape of the functions describing how threshold amplitude decreases as a function of pulse duration for single pulses (FIG. 21A) and how threshold increases as a function of pulse pair separation (FIG. 21B). Estimates of $\tau_1$ in our model varied between 0.24-0.65 ms, with a mean of 0.42 ms, a value very similar to electrophysiology estimates of the integration of current by ganglion cells. Extracellular electrical stimulation of retinal ganglion soma results in measured time constants that vary between 0.22 ms and 0.51 ms (Jensen et al., 2005a; Fried et al., 2006; Sekimjak et al., 2006). It should be noted that intracellular current injection seems to result in much slower time constants (O'Brien et al., 2002), that were greater than 3.9 ms. One possibility is that the time constant of extracellular stimulation is based on the activation of the sodium channel current in ganglion cells, which is on the order of 0.1 ms, rather than upon the time constant of the entire membrane (Litpon, 1987). In contrast, the time constants of bipolar and amacrine cells are estimated to be far slower. It is thought that the long-latency spiking in ganglion cells, occurring >8-60 ms after the beginning of electrical stimulation (Greenberg, 1998; Jensen et al., 2005a; Fried et al., 2006), probably originates from bipolar cells since a cocktail of synaptic blockers completely suppresses this late-phase spiking in ganglion cells. The measured time constant associated with these longer latency spikes varies between 20-26 ms, depending on electrode size. The time constant associated with the inhibitory input from amacrine cells is on the order of 100-200 ms (Fried et al., 2006). The similarity of $\tau_1$ to time constants of current integration by ganglion cells suggests that direct stimulation of ganglion cells (rather than indirect stimulation via pre-synaptic input) may be primarily responsible for integration of stimulation current within the retina. $\epsilon$ and $\tau_2$ (Eq. 3) The parameters $\epsilon$ and $\tau_2$ represent desensitization as a consequence of accumulated charge, where $\epsilon$ represents the strength of desensitization and $\tau_2$ represents the time constant over which charge was integrated. The values $\epsilon$ and $\tau_2$ were mainly determined by the difference in the data curve slopes between the 0.075 and 0.975 ms pulse trains as a function of frequency for both threshold and suprathreshold data (FIGS. 21C & D, FIG. 22). As frequency increases there is a decrease in the amount of current needed, per pulse, to reach threshold. However, the slope of this decrease was steeper for 0.075 than for 0.975 ms pulses, consistent with desensitization as a function of accumulated charge. $\epsilon$ ranged from 2 to 3 with a mean of 2.25 for threshold stimulation, and between 8 to 10 with a mean of 8.73 for suprathreshold stimulation. Estimates of $\tau_2$ ranged between 38 and 57 ms with a mean of 45.25 ms.

There are two possible sources for this change in sensitivity as a function of previous charge. One possibility is that injected charge directly results in a hyperpolarization of membrane resting potentials within individual ganglion cells. Shifts in resting potentials that seem to be analogous to slow contrast adaptation effects, can be produced in ganglion cells by injection of hyperpolarizing current (Baccus and Meister, 2002). However it is also likely that inhibition from presynaptic cells plays a role in the desensitization we observed. Inhibitory presynaptic influences on spiking in response to electrical stimulation have been described by Fried et al. (Fried et al., 2006), especially for longer pulses. It seems likely that the desensitization stage of our model simply approximates a series of complex adaptive processes, with time courses varying between milliseconds to tens of seconds (Chander and Chichilnisky, 2001; Rieke, 2001; Baccus and Meister, 2002), occurring both in the retina and beyond. $\beta$ (Eq. 4). The parameters $\beta$ describes an expanding input-output nonlinearity. Power nonlinearities have been proposed in a variety of linear-nonlinear models developed to describe spiking as a function of contrast in single ganglion cells (Chander and Chichilnisky, 2001; Baccus and Meister, 2002). A similar nonlinearity has also been used to model human behavioral data describing the perceptual temporal integration of light stimuli (Watson, 1986). In the case of our model and that of Watson, this power function presumably describes the input-output nonlinearity across a population of cells. $\beta$ was constrained by the slopes describing the decrease in the amount of current required to reach threshold or a given level of brightness with increasing frequency (FIG. 21C-G, FIG. 22). $\beta$ varied between 3.0-4.2, with a mean of 3.43 for threshold stimulation. Lower values of $\beta$ were required to fit suprathreshold data. Depending on the brightness level, values of β ranged between 0.6-1.0, with a mean of 0.83. An increase in the brightness of the percept to be matched led to a decrease in the slope of the response nonlinearity. One possibility is that as the intensity of stimulation increases, neurons with shallower input-output nonlinearities are recruited. Alternatively, this change in the power function may be driven by changes in the input-output nonlinearity within individual cells. It has been found in models of retinal spiking that the slope of the nonlinearity changes as a function of increased contrast (Rieke, 2001; Baccus and Meister, 2002). $\tau_3$ (Eq. 5) The parameter $\tau_3$ determines the integration period of the final low pass filter. This time constant was primarily determined by the shapes of the curves of (FIG. 21E-G). Thresholds decrease as a function of frequency for a fixed number of pulses, with an asymptote at around 100-200 Hz, with the effect being most noticeable for the pulse train containing 15 pulses. (At frequencies above 1000 Hz there was a slight increase in threshold, in our model which was due to the first integration time constant, $\tau_1$.) $\tau_3$ was found to range between 24-33 ms, with a mean of 26.25 ms. It is possible that $\tau_3$ may represent the slow temporal integration that occurs in cortex: similar integration times have been found in simple cell recordings in cat striate cortex (Reid et al., 1992), and Watson's model of a wide range of psychophysical data examining the integration of temporal light stimuli requires an analogous second-stage low-pass filter with a roughly similar time constant (Watson, 1986).

The power of this model was significantly higher than that of a less constrained model where $\tau_1$, $\tau_2$, $\tau_3$, ε and β were all allowed to vary across each experiment and electrode (F test, $F_{ratio}=0.2501$, α<0.01). While there were some small deviations between the model and the data, these deviations were relatively small compared to comparable models of psychophysical performance for temporal light stimuli e.g. (Watson, 1986; Foley and Boynton, 1994). There were some systematic deviations between the model and performance for long pulses at suprathreshold levels of stimulation (FIGS. 22 B&C). It is perhaps not surprising that our model did not generalize completely to suprathreshold levels of stimulation with long pulses given that neurophysiological data suggests that presynaptic cells will have a much larger influence on neuronal responses to such stimuli (Fried et al., 2006).

This model is also highly constrained compared to analogous models that have been used to model human responses to temporally varying light patterns e.g. (Watson, 1986; Foley, 1994). In these psychophysical models a similar number of parameters are required, a smaller range of temporal patterns are generally modeled, and parameters are typically allowed to vary across subjects. This model is also constrained relative to a similar model of temporal sensitivity in cochlear implants (Shannon, 1989) where once again, a similar number of parameters was required, a smaller range of temporal patterns was modeled, and parameters were allowed to vary across subjects. Finally, this model is constrained compared to similar models that have been used to describe the spike timing response of retinal ganglion cells (Chander and Chichilnisky, 2001; Rieke, 2001; Baccus and Meister, 2002). In these models a similar number of parameters are required to describe cell responses, a smaller range of temporal patterns are modeled, and parameters of the model are allowed to vary across each individual cell.

Achieving useful percepts requires satisfying a variety of safety and engineering constraints. First, we assume that useful percepts require stimulation at frequencies higher than subjects' perception of visible flicker (frequencies above the "critical flicker frequency"). Second, safety concerns dictate relatively stringent charge density limits, since high charge densities have the potential to compromise the integrity of electrode material (Brummer and Turner, 1975; Brummer et al., 1983) and cause damage to stimulated neural cells (McCreery et al., 1988; McCreery et al., 1990; Shannon, 1992). Third, the maximum current amplitude that can be produced may in some cases be limited by the compliance voltage of the stimulator. A final set of constraints include limits in the amount of power available to the implant given the need for a long battery life, and power limits inherent in transmitting power inductively, resulting in a need to minimize overall charge.

Figure 26A:
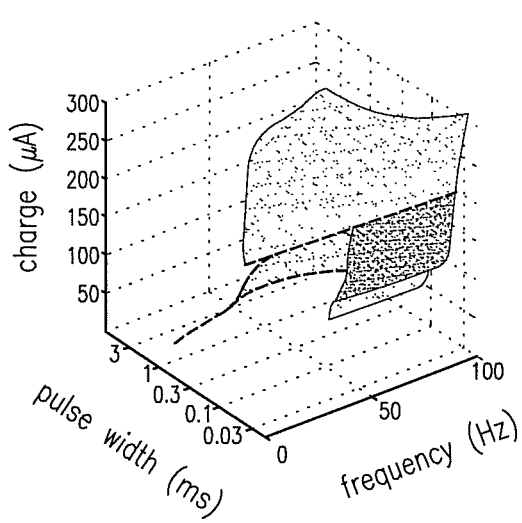
FIG. 26 A-C are summary charts showing the stimulation response predictions resulting from the preferred model.
Figure 26B:
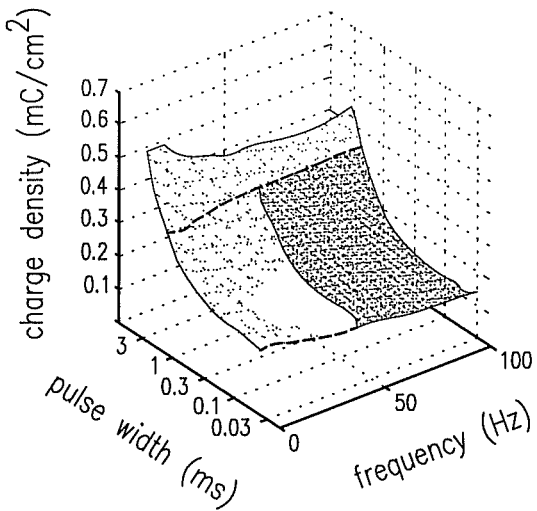
Figure 26C:
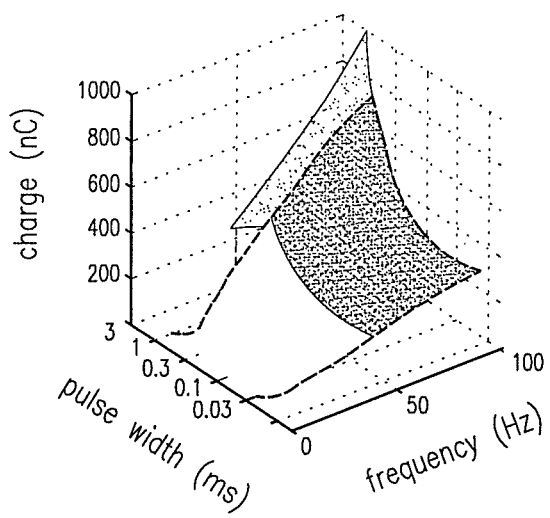

Our model allows us to determine the optimal stimulation pattern needed to produce a percept of a given brightness level given these constraints. FIG. 26 shows example predictions of threshold current amplitude (FIG. 26A), charge density (FIG. 26B), and overall charge (FIG. 26C) for a 500 ms pulse train presented on an electrode of typical sensitivity across a range of pulse widths and frequencies. The dashed lines represent examples of safety and engineering constraints that might restrict the potential set of stimulation patterns. We assumed that stimulation must be at a rate higher than a critical flicker frequency of 50 Hz (Graham, 1965), a current amplitude limit of 200 μAmps, and a charge density limit of $0.35 mC/cm^2$. Given these example constraints, our model predicts that the most charge efficient stimulation pattern is a 50 Hz pulse train consisting of 0.089 ms pulses. Of course this ability to evaluate engineering and safety trade-offs across different pulse patterns need not be restricted to simple stimulation patterns such as those used in this example.

We report here the first quantitative model of the perceptual effects of electrical retinal stimulation in retinitis pigmentosa patients. Visual perceptual responses could be predicted with a surprisingly simple model that bears a close resemblance to models of ganglion cell firing behavior during contrast adaptation (Chander and Chichilnisky, 2001; Rieke, 2001; Baccus and Meister, 2002), human temporal integration of light stimuli (Watson, 1986), and auditory processing in cochlear implant users (Shannon, 1989).

Models such as ours may provide some insight into the neural pathways responsible for responding to electrical stimulation. The integration time course of the first stage ($\tau_1$) of our model supports electrophysiology data (Jensen et al., 2005b, a) suggesting that direct stimulation of ganglion cells may be the primary source of percepts in epiretinal electrical stimulation. The need to include desensitization as a function of charge in our model suggests that processes similar to those found in contrast gain control for light stimuli (Chander and Chichilnisky, 2001; Rieke, 2001; Baccus and Meister, 2002) may also occur during electrical stimulation, consistent with electrophysiology data on the effects of injecting hyperpolarizing current from Baccus and Meister (Baccus and Meister, 2002). Finally, the time constant of the final stage of our model is consistent with the slow integration time periods found within cortex (Watson, 1986; Reid et al., 1992), suggesting that this stage of our model may represent cortical rather than retinal processes.

A successful retinal prosthesis will need to produce percepts consisting of regions of constant brightness and across a range of brightness levels, while satisfying a complex set of engineering constraints: charge densities must remain relatively low, it is technically difficult to produce very high current amplitudes, and absolute charge must be minimized to maximize battery life. Models of the perceptual effects of electrical stimulation, such as that described here, will be critical in allowing electrical stimulation protocols to be selected that best satisfy these many constraints.

Of course, a wide variety of challenges remain. For example, apparent brightness is not the only perceptual quality that needs to be considered. It is possible that different temporal patterns stimulate slightly different subpopulations of neurons, resulting in distinct percepts. Moreover, our experiments only considered pulse trains of relatively short duration (a maximum of a few seconds). Longer periods of continuous stimulation (minutes or hours) may result in long-term adaptation, sensitization, and/or retinal rewiring. It is quite likely that frequent electrical stimulation over a time scale of weeks and months may result in changes in retinal connectivity and responsivity (Marc et al., 2003). Additionally, it is of course of critical importance to understand how neighboring electrodes may interact in the spatiotemporal domain. Our model simply predicts sensitivity over time at the single electrode level, the extension of models such as ours to the spatial domain is an obvious next step.

Finally, a successful prosthesis will involve designing arrays which are stable on the retina, map to predictable locations in space, and are of high enough resolution to provide the quality of visual information needed to perform useful real world tasks.

Referring to FIG. 21 Each row contains an example of the pulse train stimulus (Column 1) and data (gray symbols) with model predictions from the constrained model (solid lines, see below) for patients S05 (Column 2) and S06 (Column 3). All plots are log-linear. Error bars generated using a Monte-Carlo simulation are shown (some error bars are smaller than the data symbol). These data are from electrodes C3 and A1, from patient S05 and S06, respectively. (A) Single Pulse Threshold. Stimuli were single, biphasic, charge-balanced square pulses, whose pulse width varied in duration from 0.075 ms to 4 ms (dotted arrow). Anodic and cathodic phases had equal duration and amplitude. For each pulse width, the amplitude was varied (solid arrow) to determine perceptual threshold. In the data plots, the x-axis represents pulse width and the y-axis represents the current needed to reach threshold. As pulse width increases there is an exponential decrease in the current amplitude needed to reach perceptual threshold. (B) Exp 2. Latent Addition. Stimuli were 0.075 ms pseudo-monophasic pulse pairs (the anodic phases were presented 20 ms after the end of the second cathodic pulse). The initial "conditioning" cathodic pulse always had fixed amplitude (50% of the single pulse threshold). The delay between the start of the conditioning pulse and the start of the test pulse varied between 0.15 ms and 12 ms (dotted arrow). After this variable delay, a second cathodic "test" pulse was presented. The amplitude of this test pulse was varied to determine threshold (solid arrow). In each data plot, the x-axis represents the delay between the conditioning and the test pulse. As the delay between the two pulses increases, the current necessary for the second pulse to reach threshold increases. (C & D) Short Pulse and Long Pulse Fixed Duration Pulse Train. Stimuli were 200 ms pulse trains whose frequency varied between 5 Hz and 225 Hz. In the short pulse fixed duration pulse train experiment the pulse width was 0.075 ms and in the long pulse fixed duration pulse train the pulse width was 0.975 ms. The amplitude of all pulses within the train was varied to determine threshold. In these data plots, the x-axis represents frequency and the y-axis represents the current amplitude (across all pulses) needed to reach threshold. As frequency increases there is a roughly exponential decrease in the necessary current to obtain threshold. (E, F & G) Variable Duration Pulse Train with 2, 3 or 15 Pulses. Stimuli were pulse trains whose frequency was varied between 3 Hz and 3333 Hz. Pulse trains contained 2, 3 or 15 pulses. The amplitude of all pulses within the train was varied simultaneously to determine threshold. In these data, the x-axis represents frequency and the y-axis represents the current amplitude (across all pulses) needed to reach threshold. As frequency increases, there is a decrease in necessary current to reach threshold. At extremely high frequencies there is a slight increase in threshold.

Referring to FIG. 22. (A) Suprathreshold—Short Pulse (2 times threshold). Stimuli were 200 ms pulse trains consisting of 0.075 ms pulses, whose frequency varied between 5 Hz and 135 Hz. The amplitude value for the 5 Hz train was set at 2 times threshold and the amplitude of the 15 Hz pulse train was modulated to find the amplitude that was equally bright to that of the 5 Hz pulse train. We then obtained an isobrightness curve for frequencies from 5 Hz to 135 Hz, as described in the main text. The black line represents the prediction of our model. In general, there is a decrease in necessary current per pulse to reach equibrightness as frequency increases. (B) Suprathreshold—Long Pulse (2 times threshold). Stimuli were 200 ms pulse trains consisting of 0.975 ms pulses, whose frequency was varied between 5 Hz and 135 Hz. Again, there is a decrease in necessary current per pulse as frequency is increased. (C) Suprathreshold—Long Pulse (3 times threshold). Here the amplitude of the 5 Hz train was set to 3 times the threshold value. Again, there is a decrease in necessary current per pulse as frequency is increased. Data for 3 times threshold was not collected for short pulse trains because this would have required stimulating above safety limits.

Figure 23:
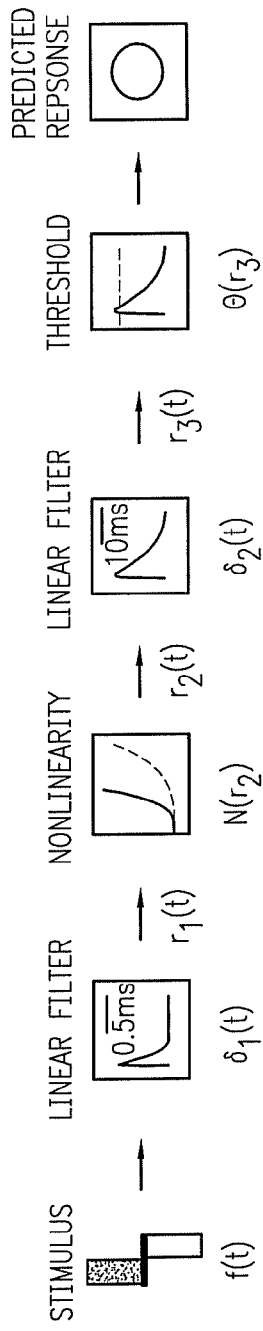
FIG. 23 is a flow chart showing the preferred model
Figure 24A:
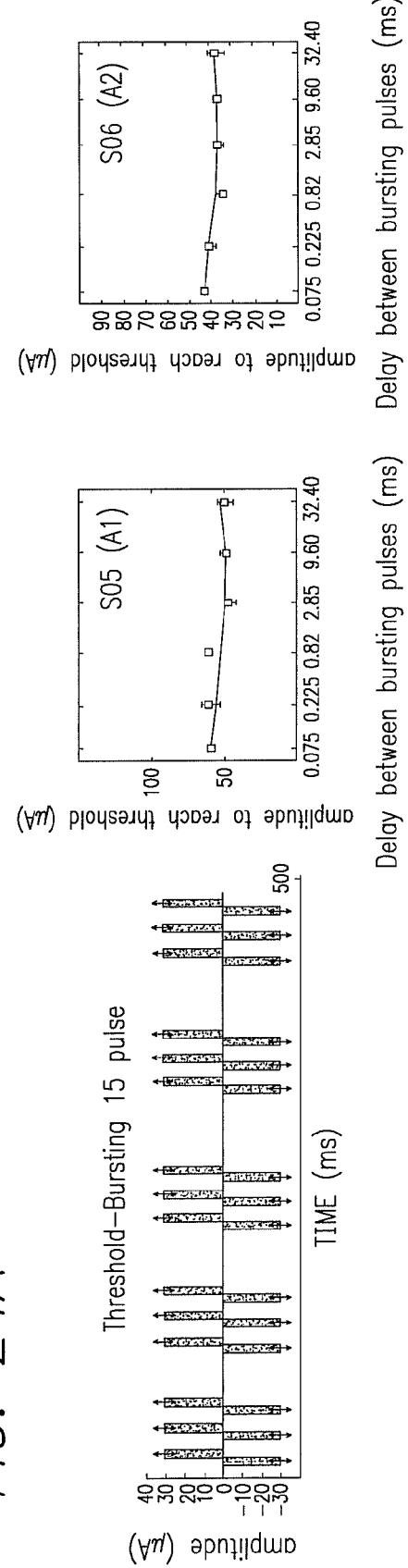
FIG. 24 A-C is a series of bar charts and response graphs where each row shows a novel pulse train stimulus and data with model predictions from the constrained model.
Figure 23A:
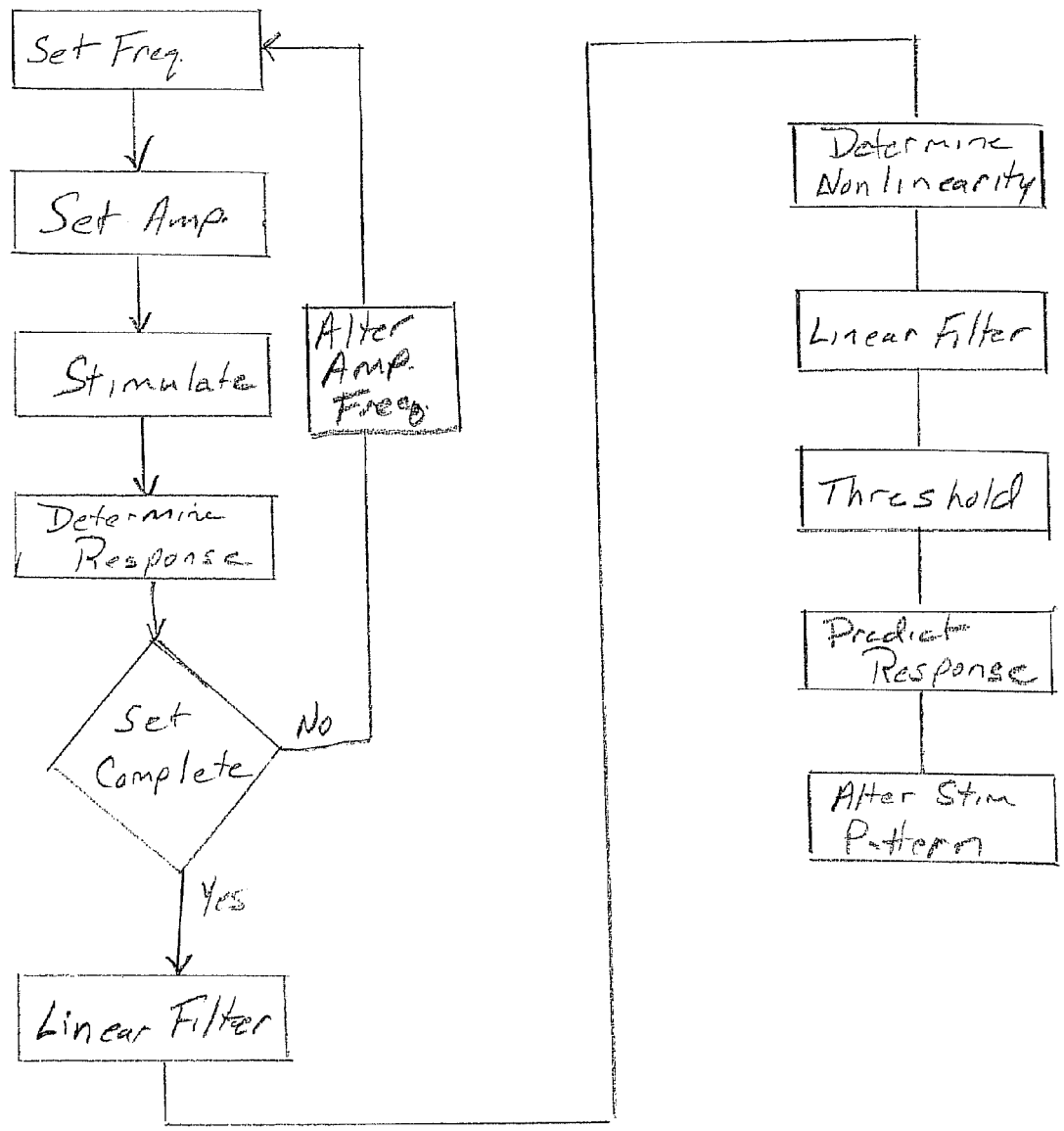
FIG. 23A is the flow chart of FIG. 23 in more detail.
Figure 24B:
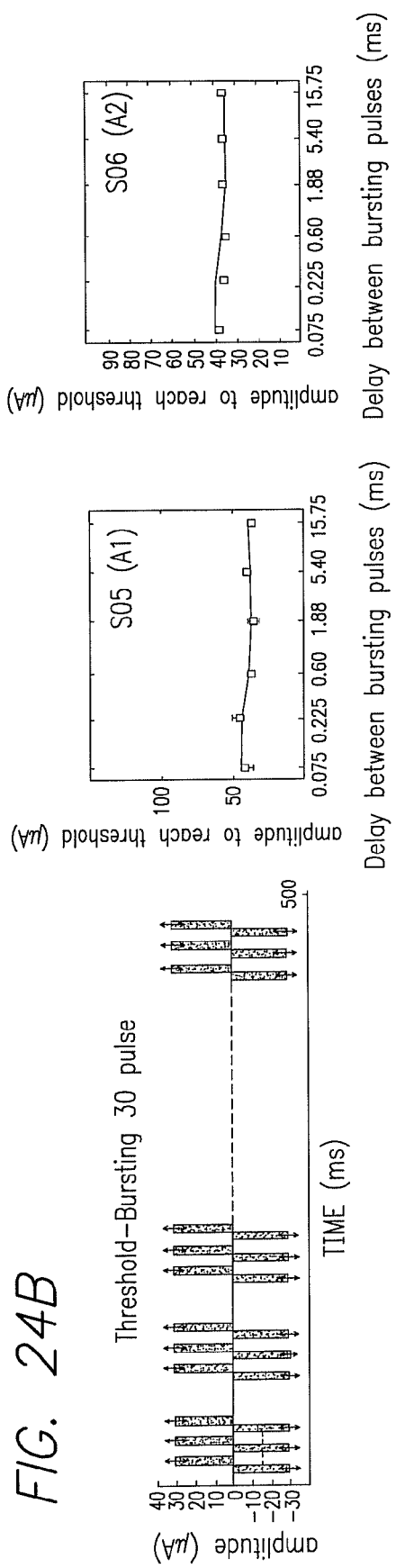
Figure 24C:
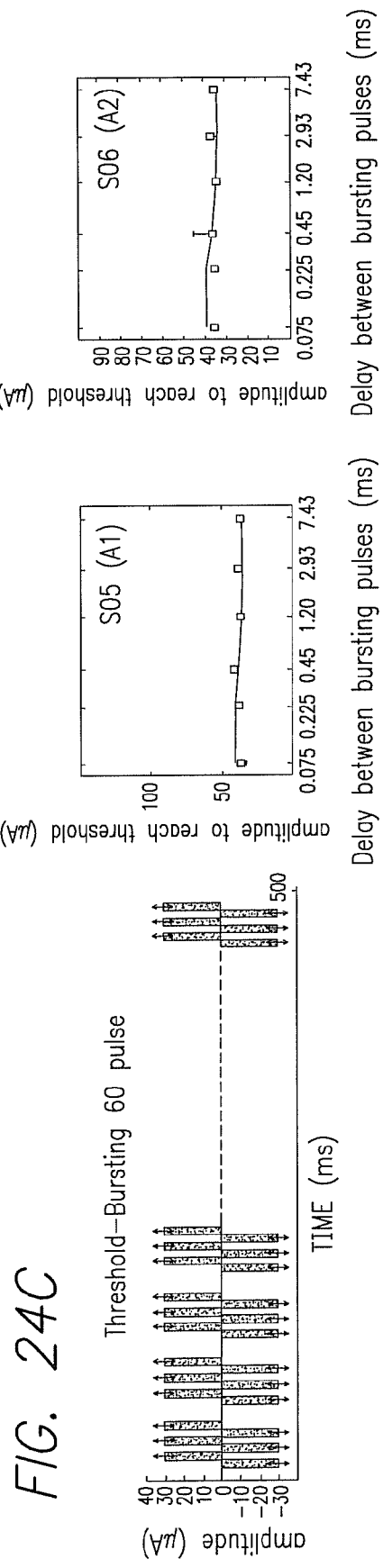
Figure 25C:
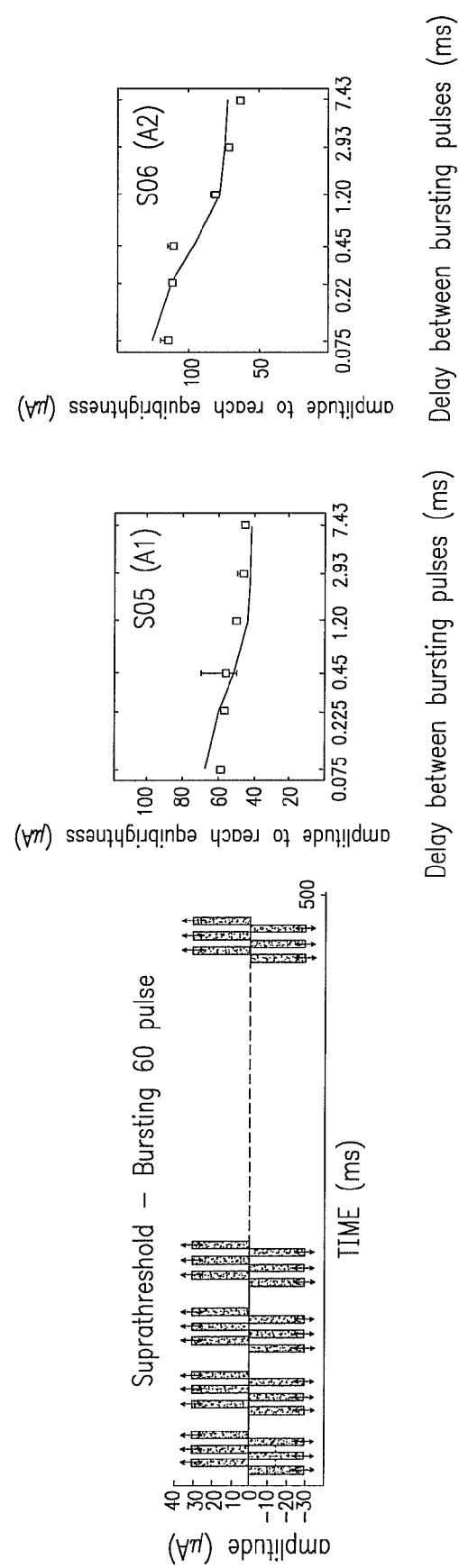
FIG. 25 A-C is a series of bar charts and response graphs where each row shows a novel pulse train stimulus and data for suprathreshold responses with model predictions from the constrained model.

FIG. 23 is a schematic of the model. The signal input is convolved with a 1-stage linear filter (Eq. 1). The signal is then passed through a shifting, power nonlinearity (Eqs. 3 & 4), where the shift depends on the amount of previously presented charge within the pulse train and the slope of the nonlinearity depends on the extent to which the stimulus us above threshold (see below). The output of the nonlinearity is then convolved with a 3-stage linear filter with a much longer time constant (Eq. 5). Finally, we assumed that a stimulus was at visual threshold (or a given brightness level) when its final response reached a threshold value (Eq. 6).

Referring to FIG. 24, each row contains an example of the novel pulse train stimulus (Column 1) and threshold data with model predictions for patients S05 (Column 2) and S06 (Column 3). All pulse trains consisted of a 500 ms pulse train consisting of bursts of three pulses. Each burst consisted of 0.45 ms biphasic pulses with no inter-phase delay. The x-axis represents the delay between each set of 3 bursting pulses. A) Threshold Bursting—15 Pulse. Stimuli consisted of 5 bursts. The inter pulse delay between each of the three pulses in each burst varied between 0.075-32.4 ms. For the 32.4 ms inter pulse delay the pulses were evenly distributed throughout the 500 ms time period of stimulation. This inter pulse delay is represented on the x-axis. The y-axis is the current needed to reach perceptual threshold. (B) Threshold Bursting—30 Pulse. Stimuli consisted of 10 bursts. The inter pulse delay between each of the three pulses in each burst varied between 0.075-15.75 ms, with the pulses evenly distributed throughout the 500 ms time period of stimulation for the 15.75 ms inter pulse delay. (C) Threshold Bursting—60 Pulse. Stimuli consisted of 20 bursts. The inter pulse delay between each of the three pulses in each burst varied between 0.075-7.425 ms, with the pulses evenly distributed throughout the 500 ms time period of stimulation for the 7.425 ms inter pulse delay.

Referring to FIG. 25, each row contains an example of the pulse train stimulus (Column 1) and suprathreshold data with model predictions for patients S05 (Column 2) and S06 (Column 3). All pulse trains consisted of a 500 ms pulse train consisting of bursts of three pulses. Each burst consisted of 0.45 ms biphasic pulses with no inter-phase delay. The x-axis represents the inter-pulse delay between the set of 3 bursting pulses. A) Suprathreshold Bursting—15 Pulse. Stimuli consisted of 5 bursts. The inter pulse delay between each of the three pulses in each burst varied between 0.075-32.4 ms. For the 32.4 ms inter pulse delay, the pulses were evenly distributed throughout the 500 ms time period of stimulation. This inter pulse delay is represented on the x-axis on log axes. The y-axis is the current needed to reach visual threshold. (B) Suprathreshold Bursting—30 Pulse. Stimuli consisted of 10 bursts. The inter pulse delay between each of the three pulses in each burst varied between 0.075-15.75 ms, with the pulses evenly distributed throughout the 500 ms time period of stimulation for the 15.75 ms inter pulse delay. (C) Suprathreshold Bursting—60 Pulse. Stimuli consisted of 20 bursts. The inter pulse delay between each of the three pulses in each burst varied between 0.075-7.425 ms, with the pulses evenly distributed throughout the 500 ms time period of stimulation for the 7.425 ms inter pulse delay.

Referring to FIG. 26 Model predictions of threshold for a 500 ms pulse train for a typical electrode. In each panel the x-axis represents pulse width on a logarithmic axis, and the y-axis represents frequency. Red dashed lines represent a current amplitude limit of 200☐☐mps, yellow dashed lines represent the constraint that stimulation must occur above the critical flicker frequency of 50 Hz, and blue dashed lines represent the constraint of a charge density limit of 0.35mC/$cm^2$. Light shading represents pulse widths and frequencies that fall outside these constraints. The z-axis represents (A) current, (B) charge density, and (C) overall charge across the entire pulse train. Given these example constraints, our model predicts that the most charge efficient stimulation pattern is a 50 Hz pulse train consisting of 0.089 ms pulses, as shown by a * in Panel C.

In summary, a process for designing an apparatus and a method for stimulating neural tissue is provided. The apparatus provides a means for adjusting the RF link to the internal coils, and the method provides the maximum intensity with minimum current by modeling responses to varying stimulation parameters including frequency, pulse width, and pattern of pulse series (trains).

Accordingly, what has been shown is an apparatus and method for stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual stimulation method, comprising:
generating a first series of stimulation patterns by stimulating neural tissue of a patient with a series of impulsive electrical signals with varying stimulation amplitude;
determining a relationship of stimulation amplitude to induced phosphene brightness in response to said first series of stimulation patterns;
generating a second series stimulation patterns by stimulating neural tissue of a patient with a series of impulsive electrical signals, wherein said second stimulation pattern alters frequency;
predicting how induced phosphene brightness depends on the second series of stimulation patterns by estimating perceptual threshold as an exponential function of stimulation frequency versus stimulation amplitude based on stimulation with a time constant of less than 1 ms; and
altering further stimulation amplitude and frequency based upon a prediction derived from the step of predicting.

2. The method of claim 1, wherein said first and second series of stimulation patterns include biphasic pulses with a pulse width that varies between 0.075 ms and 4 ms.

3. The method of claim 1, wherein said determining a relationship of stimulation amplitude to induced phosphene brightness comprises evaluating stimulation amplitude to reach perceptual threshold as a function of pulse width to find that stimulation amplitude to reach perceptual threshold decreases as pulse duration increases.

4. The method of claim 3, wherein pulse width is made variable between 0.075 ms and 4 ms.

5. The method of claim 3, further comprising a delay between pulses, wherein said delay is variable and said variable delay varies between 0.075 ms and 300 ms.

6. The method of claim 1, wherein said determining a relationship of stimulation amplitude to induced phosphene brightness comprises applying a leaky integrator model.

7. The method of claim 1, wherein said determining a relationship of stimulation amplitude to induced phosphene brightness comprises evaluating summation across at least on pulse pair in function of stimulation amplitude to reach perceptual threshold to determine how a first pulse of the at least one pulse pair contributes to a perceptual threshold response of a second pulse of the at least one pulse pair.

8. The method of claim 1, wherein said determining a relationship of stimulation amplitude to induced phosphene brightness comprises
applying a linear filter to said first series of stimulation patterns,
measuring a perceptual threshold, and
comparing said perceptual threshold with a predicted perceptual threshold response based upon said frequency.

9. The method of claim 1, wherein said a relationship of stimulation amplitude to induced phosphene brightness comprises
applying a non-linear filter to said first second series of stimulation patterns,
measuring a perceptual threshold, and
comparing said perceptual threshold with a predicted perceptual threshold response based upon said frequency.

10. The method of claim 1, wherein said determining a relationship of stimulation amplitude to induced phosphene brightness comprises
applying a linear filter to said first and second series of stimulation patterns,
measuring a non-linearity in a signal resulting from said step of applying a linear filter to said first and second series of stimulation patterns, and
comparing said non-linearity with a predicted response based upon said frequency.

11. The method of claim 1, wherein said determining a relationship of stimulation amplitude to induced phosphene brightness comprises
applying a first linear filter o said first and second series of stimulation patterns,
measuring a non-linearity in a signal resulting from said step of applying a linear filter to said first and second series of stimulation patterns,
applying a second linear filter,
measuring a perceptual threshold, and
comparing said perceptual threshold with a predicted response based upon said frequency.

12. The method of claim 11, wherein said second linear filter is convolved with said measured non-linearity.

13. The method of claim 1, wherein the determining a relationship of stimulation amplitude to induced phosphene brightness comprises evaluating amplitude to reach perceptual threshold in function of pulse train frequency to find that current amplitude to reach perceptual threshold decreases as pulse train frequency increases.

14. The method of claim 13, further comprising evaluating whether decrease of stimulation amplitude to reach perceptual threshold also depends on number of pulses.

15. The method of claim 13, wherein said evaluating stimulation amplitude to reach perceptual threshold in function of pulse train frequency comprises evaluating plural pulse trains.

16. The method of claim 15, wherein the plural pulse trains comprise a first pulse train with two pulses, a second pulse train with three pulses, and a third pulse train with fifteen pulses.

17. The method of claim 16, further comprising a delay between pulses of each pulse train wherein the delay varies between 0.075 ms to 300 ms.

18. The method of claim 16, wherein at a pulse train frequency of less than 50 Hz, the perceptual threshold depends on a delay between pulses.

19. The method of claim 1, wherein stimulating neural tissue is stimulating visual neurons.

\* \* \* \* \*